United States Patent [19]

Kagawa et al.

[11] Patent Number: 5,163,433
[45] Date of Patent: Nov. 17, 1992

[54] ULTRASOUND TYPE TREATMENT APPARATUS

[75] Inventors: Hiroaki Kagawa; Tomohisa Sakurai; Tetsumaru Kubota; Hitoshi Karasawa, all of Hachioji; Tatsuya Kubota, Sagamihara; Yuichi Ikeda, Hachioji; Mitsumasa Okada, Hachioji; Toshihiko Suzuta, Hachioji; Hideo Nagazumi, Hachioji; Kazuya Hijii, Hachioji; Masahiro Kudo, Hachioji; Kenji Yoshino, Tama; Tadao Hagino, Yokohama, all of Japan

[73] Assignee: Olympus Optical Co., Ltd., Tokyo, Japan

[21] Appl. No.: 780,130

[22] Filed: Oct. 21, 1991

Related U.S. Application Data

[63] Continuation-in-part of Ser. No. 573,673, Aug. 24, 1990, Pat. No. 5,076,276.

[30] Foreign Application Priority Data

| | | | |
|---|---|---|---|
| Nov. 1, 1989 | [JP] | Japan | 1-285700 |
| Nov. 7, 1989 | [JP] | Japan | 1-129854[U] |
| Nov. 7, 1989 | [JP] | Japan | 1-289652 |
| Jan. 11, 1991 | [JP] | Japan | 3-2348 |
| Oct. 9, 1991 | [JP] | Japan | 3-261914 |

[51] Int. Cl.⁵ .................................. A61B 17/20
[52] U.S. Cl. .................... 128/660.01; 128/24 AA; 604/22; 604/27; 606/128
[58] Field of Search ............... 128/660.01, 24 AA; 604/22, 27; 73/861.18; 606/128

[56] References Cited

U.S. PATENT DOCUMENTS

| | | | |
|---|---|---|---|
| 4,516,398 | 5/1985 | Wuchinich | 604/22 |
| 4,750,488 | 6/1988 | Wuchinich et al. | 604/22 |
| 4,750,902 | 6/1988 | Wuchinich et al. | 128/24 AA |
| 4,861,332 | 8/1989 | Parisi | 128/24 AA |
| 4,867,141 | 9/1989 | Nakada et al. | 128/24 AA |
| 5,038,756 | 8/1991 | Kepley | 128/24 AA |
| 5,058,570 | 10/1991 | Idemoto et al. | 128/24 AA |

Primary Examiner—Kyle L. Howell
Assistant Examiner—George Manuel
Attorney, Agent, or Firm—Frishauf, Holtz, Goodman & Woodward

[57] ABSTRACT

An ultrasound type treatment apparatus includes an inner sheath covering an ultrasonic transmission member having a first suction passage and defining a space relative to the ultrasound transmission member and an outer sheath covering the inner sheath and defining a space relative to the inner sheath. In the treatment apparatus, a liquid medium supply passage is provided at one of the space between the ultrasound transmission member and the inner sheath and space between the inner sheet and the outer sheet to supply a liquid medium to the distal end of the ultrasound transmission member. A second suction passage is formed at the other of the space between the ultrasound transmission means and the inner sheath and space between the inner sheath and the outer sheath. The first suction passage is connected by a suction tube to the second suction passage.

12 Claims, 20 Drawing Sheets

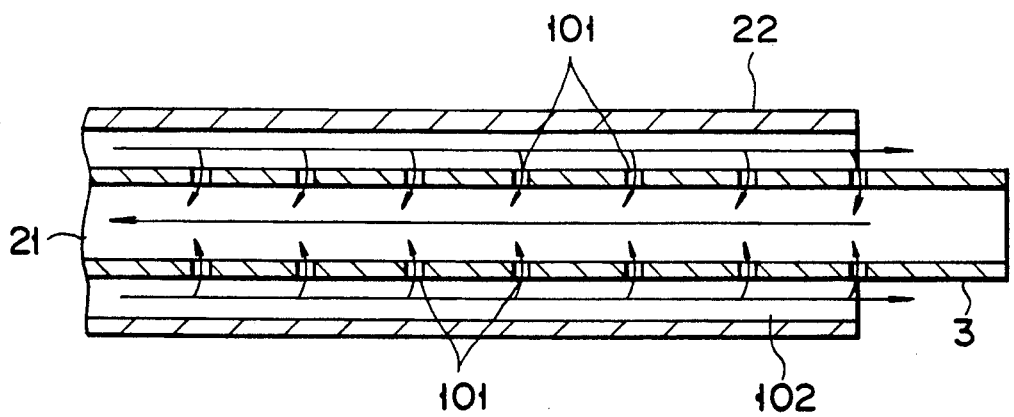
F I G. 16
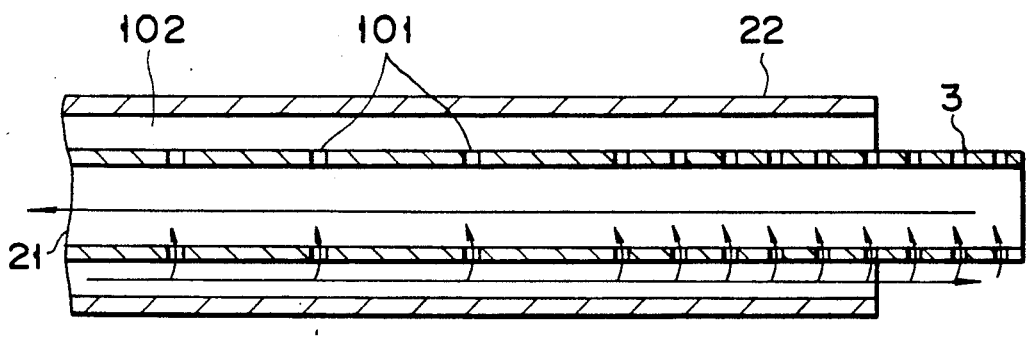
F I G. 17
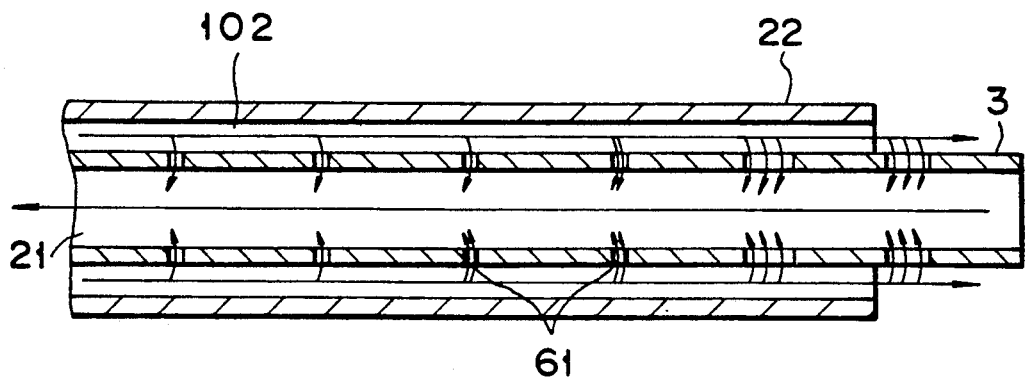
F I G. 18

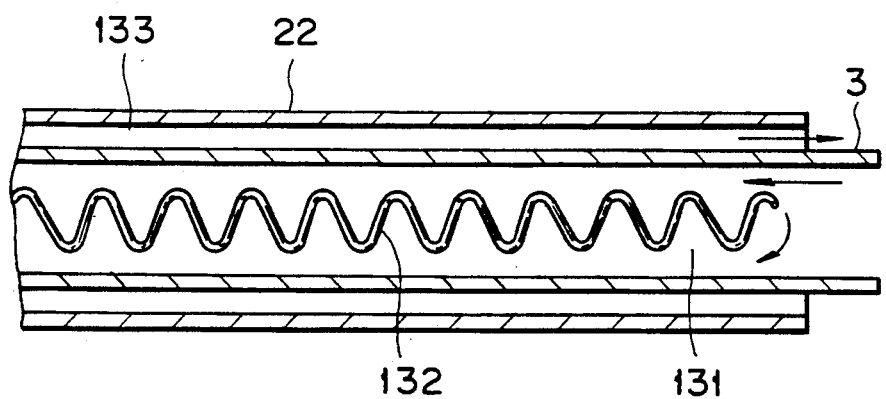
F I G. 28
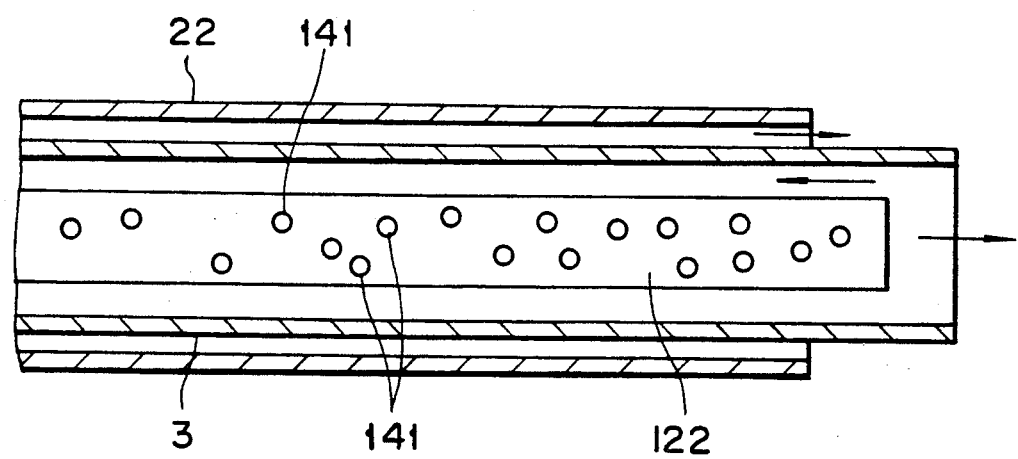
F I G. 29

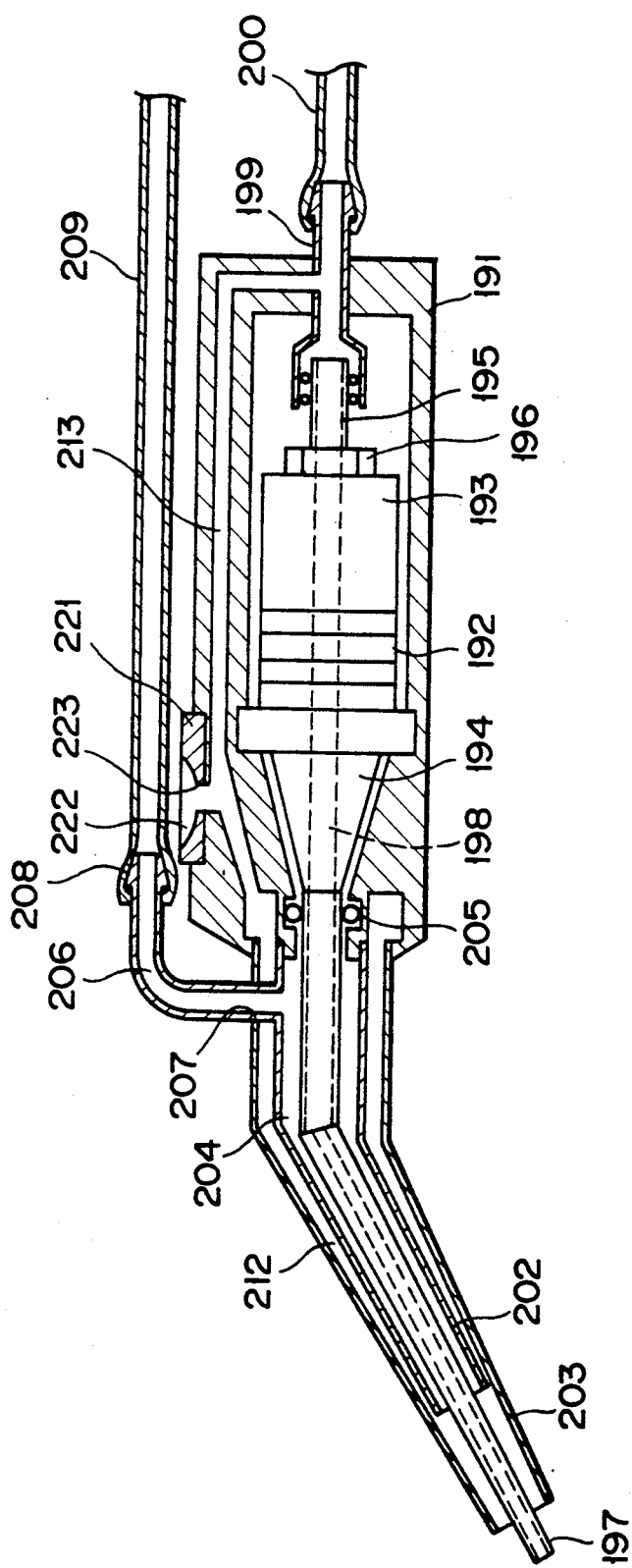
F I G. 36

_ULTRASOUND TYPE TREATMENT APPARATUS_

CROSS-REFERENCE TO THE RELATED APPLICATION

This application is a continuation-in-part of U.S. application Ser. No. 573,673 filed on Aug. 24, 1990, now U.S. Pat. No. 5,076,276 issued on Dec. 31, 1991.

BACKGROUND OF THE INVENTION

1. Field of the Invention

The present invention relates to an ultrasound type treatment apparatus used for the resection of a living tissue or the fracture of a stone in the body cavity of a human being.

2. Description of the Related Art

Generally, this type of treatment apparatus amplifies an ultrasonic oscillation, generated from an ultrasonic oscillation element, by a horn and transmits it to an ultrasound transmission member. The resection of the living tissue, fracture of the stone, etc., are performed with an oscillation energy of an ultrasonic wave transmitted to the distal end of the ultrasound transmission member.

In the case where the resection of the living tissue, the fracture of a stone in the body cavity, etc., are done with the use of the treatment apparatus, a liquid medium is flowed through a space defined between an ultrasound transmission member and a sheath covering the ultrasound transmission member to give an ultrasonic oscillation to an affected or diseased region while cleaning the region with the liquid medium. At the same time, the emulsified form of the living tissue or fractured stone for example is removed to an outside through a suction passage provided in the ultrasound transmission member. The liquid medium serves as a coolant for preventing the destruction of the ultrasound transmission member due to a fatigue involved.

In the aforementioned ultrasound type treatment apparatus, the liquid medium supplied from the distal end of the sheath to the diseased region is almost all atomized by the ultrasound oscillation of the ultrasound transmission member. This phenomenon prevents a field of view by the operator, such as a doctor. In the microsurgery under the microscope, the whole field of view is blocked by the atomized liquid medium, failing to perform a microsurgery on the diseased region.

Further, if the amount of liquid medium to be supplied is reduced to an extent to which no field of observation is blocked, the cooling of the ultrasound transmission member and ultrasonic oscillation element is not adequate, failing to generate oscillation with a larger amplitude. This is liable to generate an abnormal heat generation in the ultrasonic oscillation element and a destruction of the ultrasound transmission member.

In order to eliminate such drawbacks, an attempt has been made in U.S. Pat. No. 4,516,398 to provide a leak hole near the distal end portion of the ultrasound transmission member and suck some of the liquid medium in the sheath through the leak hole.

In such an ultrasound type treatment apparatus, however, it is possible to cool the ultrasound transmission member and ultrasonic oscillation element. In this case, almost all liquid medium supplied from the distal end of the sheath gathers at the distal end of the ultrasound transmission member and atomized toward the diseased region in the foreground, failing to secure a better field of observation.

Further, since the ultrasound transmission member is usually narrowed or tapered toward its distal end and hence becomes thinner at or near its distal end. At the time of the ultrasonic oscillation, a greater axial force acts upon that area near the distal end of the ultrasound transmission member. It is, therefore, necessary to enhance the mechanical strength at or near the distal end portion of the ultrasound transmission member. If a leak hole which may cause a mechanical defect is provided at or near its distal end, the mechanical strength of the ultrasound transmission member is lowered, sometimes causing the failure of the ultrasound transmission member at or around the leak hole.

Published Unexamined Japanese Utility Model Application 61-43454 has proposed providing a leak hole at a minimum amplitude site of an ultrasound transmission member in view of the withstanding characteristic of the ultrasound transmission member.

In this case, some of a liquid medium flowed in the sheath from a base end is sucked by the leak hole provided partway of the ultrasound transmission member, leaving only a smaller amount of liquid medium available at an area between the leak hole and the distal end of the ultrasound transmission member. The ultrasound transmission member has to be cooled with such a smaller amount of liquid. Since cooling is inadequate at the distal end portion of the ultrasound transmission member, high temperature is involved at the distal end portion of the ultrasound transmission member so that a heat injury occurs at the normal living tissue near a diseased region or the ultrasound transmission member is destroyed due to its metal fatigue.

SUMMARY OF THE INVENTION

It is accordingly the object of the present invention to provide an ultrasound type treatment apparatus which can prevent a lowered field of view due to the atomization of a liquid medium and effectively cool and ultrasonic oscillation element and hence perform a surgery, by a higher-amplitude ultrasonic oscillation, with an added safety.

According to the present invention, there is provided an ultrasound type treatment apparatus comprising:
  ultrasonic oscillation means for generating an ultrasonic oscillation;
  amplifying means for amplifying the ultrasonic oscillation generated from the ultrasonic oscillation means;
  ultrasound transmission means connected to a forward end of the amplifying means and having a first suction passage therein;
  a cover member for covering an outer periphery of the ultrasound oscillation means;
  an inner sheath covering the ultrasound transmission means and defining a space relative to the ultrasound transmission means, the inner sheath having a base end extending toward the ultrasonic oscillation means and a distal end extending toward a distal end side of the ultrasound transmission means;
  an outer sheath covering the inner sheath and defining a space relative to the inner sheath, the outer sheath having a base end extending toward the ultrasonic oscillation means and a distal end extending toward the distal end side of the ultrasound transmission means;

a liquid medium supply passage provided at one of the space between the ultrasound transmission means and the inner sheath and space between the inner sheath and the outer sheath to supply a liquid medium to the distal end of the ultrasound transmission means;

a second suction passage provided at the other of the space of the ultrasound transmission means and the inner sheath and space between the inner sheath and the outer space; and connecting means for connecting the first suction passage to the second suction passage in which some of the liquid medium supplied through the liquid medium passage is turned back at or near the distal end of the ultrasound transmission means and flows sequentially through the second suction passage and connecting means into the first suction passage side whereby it is possible to cool substantially a full length of the ultrasound transmission member with the liquid medium. It is thus possible to enhance the effect with which the ultrasound transmission means and ultrasonic oscillation means are cooled, and hence to prevent an abnormal heat generation in the ultrasonic oscillation means and the destruction of the ultrasound transmission means due to a fatigue involved. By regulating the amount of liquid medium supplied and suction force of the connecting means, the atomization of the liquid medium can be prevented, enabling a surgery to be performed by an ultrasonic wave under a better field of view.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIGS. 16 to 21, each, are a side view in cross-section showing a distal end portion of a probe in a modification of the ultrasound type treatment apparatus;

FIGS. 28 and 29, each, are a side view in crosssection showing a distal end portion of a probe in a modification of the apparatus;

FIG. 36 is a side view in cross-section generally showing an ultrasound type treatment apparatus according to a seventeenth embodiment of the present invention.

DETAILED DESCRIPTION OF THE PREFERRED EMBODIMENTS

One embodiment of the present invention will be explained below with reference to FIGS. 1 and 2.

Figure 1:
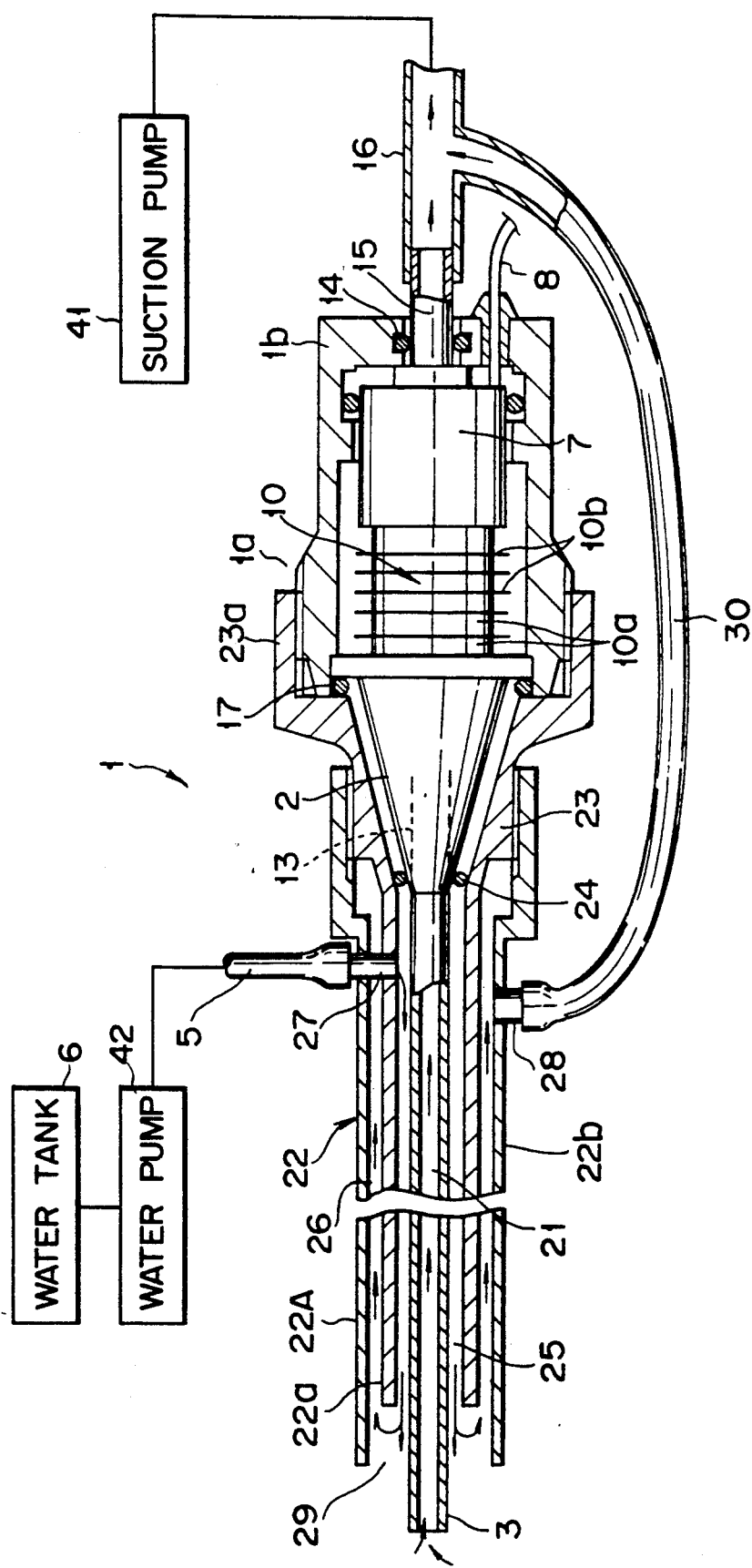
FIG. 1 is a view generally showing an ultrasound type treatment apparatus according to a first embodiment of the present invention.

In FIG. 1, reference numeral 1 shows a handpiece for an ultrasound type treatment apparatus. An ultrasonic oscillation device or element 10 is mounted in handpiece 1. A probe 3 at a location of an ultrasound transmitting means 3A is connected to the ultrasonic oscillation device 10 via a horn 2. This arrangement amplifies an ultrasonic oscillation wave of the ultrasonic oscillation device 10 at a location of the horn 2 and transmits it to the probe 3. The horn 2 and probe 3 are covered with a sheath 22 serving as a cooling water communication means as will be set forth below.

A cover 1b of a substantially bottomed-cylindrical configuration is provided at a grip section 1a of the handpiece 1 and the ultrasonic oscillation device 10 is mounted within the cover 1b.

The ultrasonic oscillation device 10 is composed of a laminated structure of piezoelectric elements (for example PZT) 10a and electrodes 10b. The horn 2 for amplifying the amplitude of the ultrasonic wave is connected to the forward end of the ultrasonic oscillation device 10. A back-up plate 7 is connected to the rear end of the ultrasonic oscillation device 10. Between the horn 2 and the back-up plate 7 the ultrasonic oscillation device 10 is fastened by a combination of a bolt, not shown, penetrating the back-up plate 7 and ultrasonic oscillation device 10 and an associated threaded nut to provide an integral structure. A power supply cord 8 is connected to the electrode 10b of the ultrasonic oscillation device 10.

A suction hole 13 is formed in the center of the horn 2 and in the bolt extending through the ultrasonic oscillation device 10 and back-up plate 7 to provide an axial communication hole. The rear end of the suction hole 13 is connected to a first suction tube 16 via a suction connector 15 extending through the rear end wall (bottom wall) of the cover 1b. A fitting groove for an O ring 14 is formed relative to the through hole of the suction connector 15 fitted at the rear end wall of the cover 1b. The outer peripheral surface of the suction connector 15 is held, in a water-tight fashion, relative to the through hole of the cover 1b with the use of the O ring 14 fitted in the fitting groove of the suction hole 15.

The first suction tube 16 is connected to a suction pump 41. The peripheral portion of the horn 2 is held, in a water-tight fashion, by an O ring 17 which is fitted relative to the inner surface of the cover 1b of the grip section 1a. The ultrasonic oscillation device 10 is held by the O rings 14 and 17 within the cover 1b in a water-tight fashion.

The probe 3 for oscillation wave transmission is formed of a hollow metal pipe and detachably connected to the forward end of the horn 2. The hole of the probe 3 provides a first suction hole or passage 21 for communicating with the suction hole 13.

The sheath 22 for covering the probe 3 and outer peripheral portion of the horn 2 is provided at the forward end portion of the handpiece 1. The sheath 22 is formed of a double tube having an inner tubular sheath section 22a and outer tubular sheath section 22b. A cover section 23 for covering the outer peripheral portion of the horn 2 is provided integral with the proximal end portion of the inner sheath section 22a. The cover section 23 has an inner taper surface corresponding to an outer peripheral surface of the horn 2. A cylindrical section 23a is formed integral with the proximal end portion of the cover section 23. An internally threaded section is provided on the inner wall portion of the sheath section 22a to engage with an externally threaded section provided on the outer peripheral surface of the forward end portion of the cover 1b of the grip section 1a. The cover section 23 is detachably threaded over the externally threaded portion of the cover 1b of the grip section 1a. An O ring 24 is provided between the inner surface of the forward portion of the cover section 23 and the outer peripheral surface of the forward end portion of the horn 2 to achieve a water-tight seal between the two.

An internally threaded portion is provided on the proximal end portion of the external sheath section 22b so as to be detachably threaded over the externally threaded portion of the outer peripheral surface portion of the cover section 23 of the inner sheath section 22a.

The inner sheath section 22a is concentrically inserted over the probe 3 to provide a spacing. The outer sheath section 22b is similarly inserted over the inner sheath section 22a to provide a concentric array of the probe, inner sheath section 22a and outer sheath section 22b. In this case, a spacing is provided between the outer sheath section 22b and the inner sheath section 22a, and between the inner sheath section 22a and the probe 3. A water supply passage 25 is provided, as a first passage, at the spacing between the probe 3 and the inner sheath section 22a. A suction passage 26 is provided, as a second passage 26, at the spacing between the inner sheath section 22a and the outer sheath section 22b.

A water supply connector 27 and second suction connector 28 are provided near the proximal end of the sheath 22 to communicate with the water supply passage 25 and suction passage 26, respectively. One end of a water supply tube 5 is connected to the outer end of the water supply connector 27. The other end of the water supply tube 5 is connected to a cooling water tank (a water supply source) 6. A known water supply pump 42 is mounted on the cooling water tank 6. The cooling water tank 6, water supply pump 42 and water supply tube 5 provide a cooling water means 6A by which the cooling water is supplied to the water supply passage 25 for the sheath 22.

One end of the suction tube 30 is connected to the suction connector 28 and the other end of the suction tube 30 is connected partway to the suction tube 16.

Figure 2:
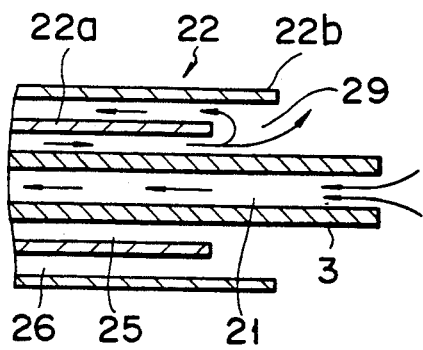
FIG. 2 is a side view in cross-section showing the distal end portion of a probe in the apparatus of FIG. 1.

The inner sheath section 22a as shown in FIG. 2 is so formed as to be shorter in length than the outer sheath section 22b with the distal end of the outer sheath section 22b extending farther than that of the inner sheath section 22a. A communication passage 29 is so provided at the distal end portion of the outer sheath section as to allow the water supply passage 25 to communicate with the suction passage 26.

The operation of the apparatus thus arranged will be explained below.

The sheath-covered probe 3 is inserted into a region of interest of a human body cavity with the grip section 1a of the handpiece 1 gripped by hand. Then a suction pump 41 is driven, applying a suction force to the first and second suction passages 21 and 26 via the first and second suction tubes 16 and 30.

The water supply pump 42 is driven, supplying water from the water supply tube 5 into the water supply passage 25 via the water supply connector 27 and then toward the distal end of the water supply passage 25. A greater quantity of water is fed into the body cavity of a human being, but some water is drawn via the communication passage 29 at the distal end portion of the sheath 22 back into the suction passage 26.

The water thus fed into the body cavity is sucked through the first suction passage 21 as shown in FIG. 2 after it has washed the body cavity clean. Any fragments of a tissue or a stone in the body cavity which are caused by the treatment of it by the probe, together with a perfused liquid, are drawn via the first suction passage 21 and also back into the first suction tube 16 through the suction hole 13.

The water sucked directly into the second suction passage 26 without being fed via the water supply passage 25 into the body cavity is supplied via the second suction tube 30, meets a stream flowing in the first suction tube 16, and is pumped back into a suction pump 41 side.

If the ultrasonic oscillation device 10 of the ultrasound type diagnostic apparatus is oscillated at a high output level and a resultant ultrasonic wave is transmitted by the probe 3, then the probe 3 is heated above a normal level. In order to prevent a temperature rise due to the generation of heat at the probe 3, a larger quantity of cooling water is flowed through the water supply passage 25. It is desirable at this time to strongly suck the water via the first suction tube 16.

If a larger quantity of water is flowed toward body cavity of the human being, an increased quantity of water is drawn via the communication passage 29 back into the second suction passage 26 upon comparison with the water flow into the body cavity. As a result, a lesser quantity of water flows into the body cavity of the human being, thus preventing a flow of a larger quantity of water into the body cavity and a flush of the water there. It is thus possible to perform an efficient diagnostic treatment without the observation field being hindered.

Further, since the second suction passage 26 is provided in addition to the first suction passage 21, it is possible to prevent a suction force from being increased to any unnecessary extent via the first suction passage 21 even under a higher suction level. This arrangement can prevent the suction of the living tissue, etc., at the distal end of the probe 3. Since the first and second suction passages 21 and 26 meet at a proximal end side, if the first suction passage 21 is clogged, then an increased amount of suction is involved and hence it is possible to prevent a living tissue, for example, from being sucked to the distal end of the probe 3.

Figure 3:
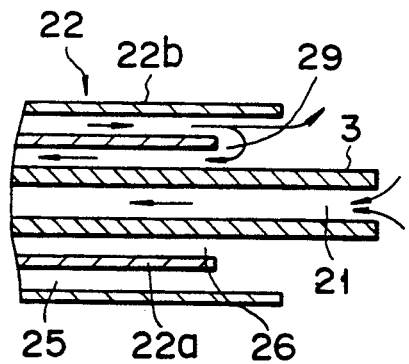
FIG. 3 is a side view in cross-section showing a distal end portion of a probe in an ultrasound type treatment apparatus according to a second embodiment of the present invention.

FIG. 3 shows a second embodiment of the present invention. In the second embodiment, a sheath 22 for covering a probe 3 is composed of inner and outer sheath sections 22a and 22b with a water supply passage 25 provided in a spacing between the inner sheath section 22a and the outer sheath section 22b. A second suction passage 26 is provided in a spacing between the inner sheath section 22a and the probe 3. The forward end of the inner sheath section 22a is shorter in length than that of the outer sheath section 22b to provide a communication passage 29. Except for this feature, the second embodiment is the same as the first embodiment.

Even in this embodiment, some of water which is supplied via the water supply passage 25 can be sucked directly from the second suction passage 26 without being supplied into a body cavity of a human being. If more water is to be supplied in order to enhance a cooling effect upon the probe 3, more water is drawn directly through the second water supply passage 26, without being sent into the body cavity, so that less water is sent into the body cavity. This prevents an accumulation of too much water in the body cavity or flushing of water there and hence prevents a restricted observation field and a subsequent lowered treatment operation.

Figure 4:
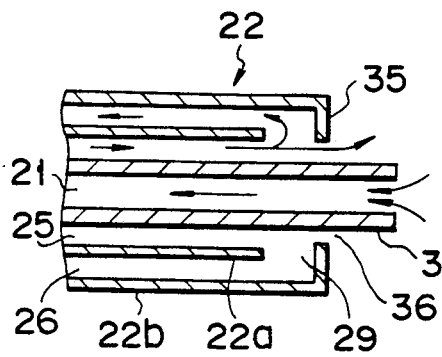
FIG. 4 is a side view in cross-section showing a distal end portion of a probe in a third embodiment of the present invention.

FIG. 4 shows a third embodiment of the present invention. In this embodiment, an inwardly projecting cover flange 35 is provided at the sheath 22 of the first embodiment such that it is located at the distal end of an outer sheath section 22b extending to a longer extent than that of the inner sheath section 22a. A gap 36 is provided between the cover flange 35 and the outer periphery of the probe 3, facilitating the ease with which water is drawn from the water supply passage 25 into a second suction passage 26 which is provided at a spacing between the inner sheath section 22a and the outer sheath section 22b. The other arrangement of the sixth embodiment is the same as that of the first embodiment.

Figure 5:
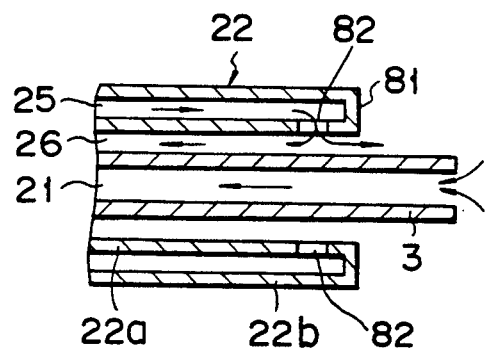
FIG. 5 is a side view in cross-section showing a distal end portion of a probe in a fourth embodiment of the present invention.

FIG. 5 shows a fourth embodiment of the present invention. In this embodiment, an end plate 81 is provided in the sheath 22 of the second embodiment (FIG. 3) such that it blocks a gap between the distal end of the inner sheath section 22a and that of the outer sheath section 22b. A plurality of water supply holes 82 are provided as passages to allow water to flow from a water supply passage 25 into a second suction passage 26 provided as a spacing between the inner sheath section 22a and the probe 3. This arrangement can facilitate ready suction of water from the water supply passage 25 into the second suction passage 26. The other arrangement is the same as that of the fifth embodiment of the present invention.

Figure 6:
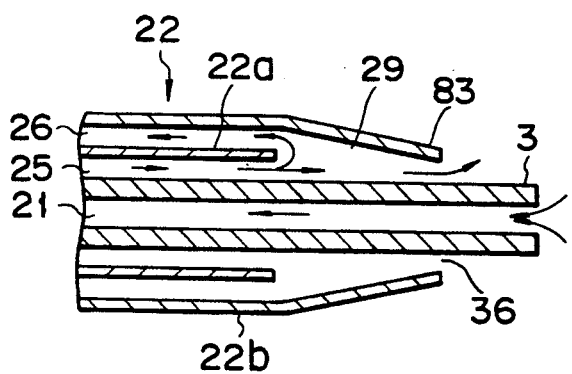
FIG. 6 is a side view in cross-section showing a distal end portion of a probe in a fifth embodiment of the present invention.

FIG. 6 shows a fifth embodiment of the present invention. In this embodiment, an inwardly directing taper cover section 83 is provided in place of the cover flange of the sheath 22 of the third embodiment (FIG. 4). A water supply gap 36 is provided between the taper cover section 83 and the outer periphery of a probe 3. Put it in another way, a second suction passage 26 is provided, without largely opening the distal end of the sheath 22, so that a suction function is facilitated in a supply of water from a water supply passage 25, into a second suction passage 26 which is defined between the inner sheath section 22a and the outer sheath section 22b. Further, since the distal end portion of the sheath 22 is tapered relative to the probe 3, it is possible to readily observe a treating end of the probe 3 in a region of interest of the human being. The other arrangement of the present invention is the same as that of the sixth embodiment of the present invention.

Figure 7:
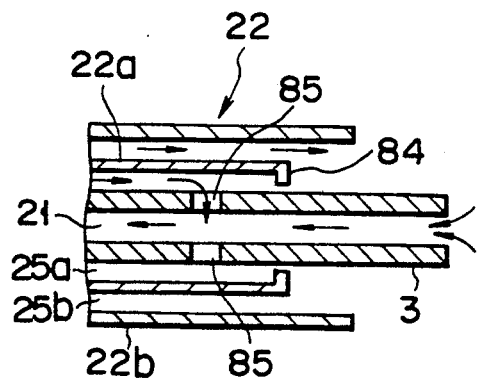
FIG. 7 is a side view in cross-section showing a distal end portion of a probe in the ultrasound type treatment apparatus.

FIG. 7 shows a modified form of a distal end portion of a probe for an ultrasound type treatment apparatus. In this modification, a water supply passage 25a is provided between an inner sheath section 22a of a sheath 22 and the outer periphery of the probe 3 and a water supply passage 25a between the inner sheath section 22a and an outer sheath section 22b. The distal end of the inner water supply passage 25a is substantially blocked by a cover flange 84 formed on the distal end of the inner sheath section 22a and projecting toward a probe 3. A plurality of communication holes 85 are formed in the distal end portion of the probe 3 to allow a suction passage 21 of the probe 3 to communicate with the inner water supply passage 25a. Since a water stream flowing through the inner water supply passage 25a is directly drawn by the communication holes 85 into the suction passage 21, it can be prevented from being flowed into a body cavity of a human being. For this reason, more water is supplied through the inner water supply passage 25a, ensuring an added cooling effect and at the same time preventing an added flow of water from the sheath into the body cavity.

Figure 8:
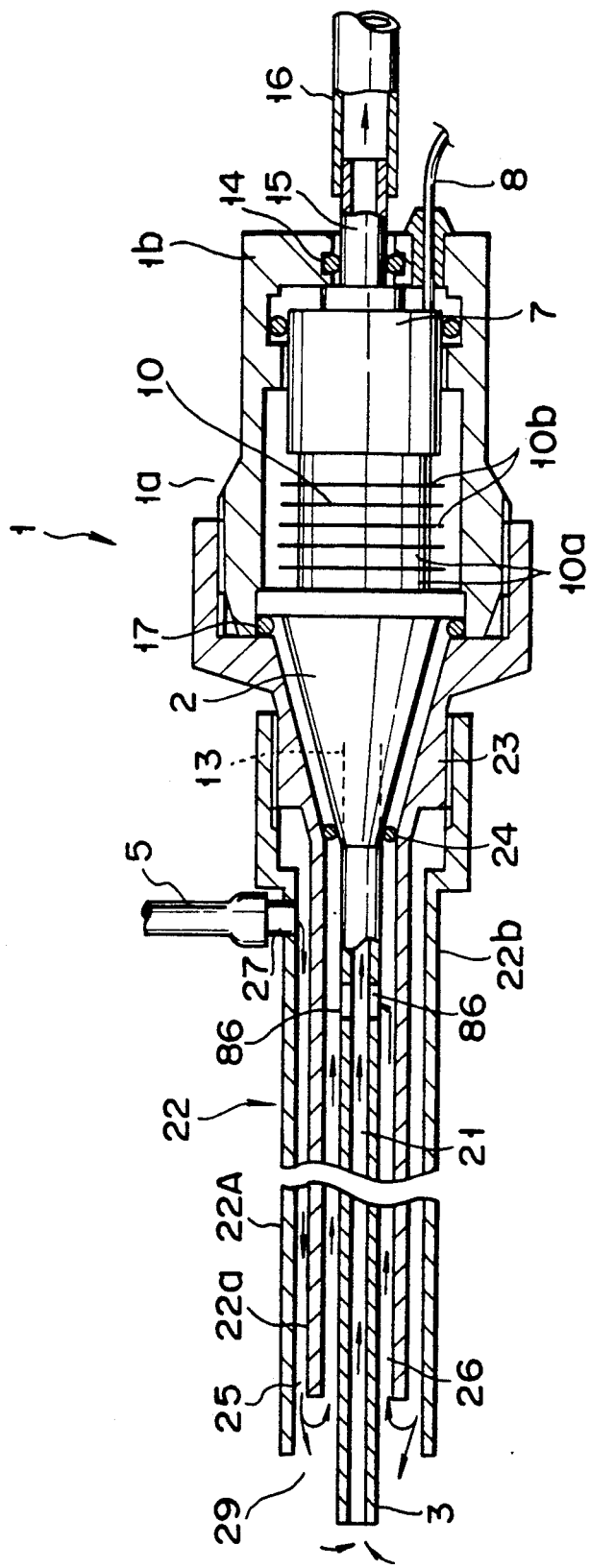
FIG. 8 is a side view in cross-section showing a sixth embodiment of the present invention.

FIG. 8 shows a sixth embodiment of the present invention. In the sixth embodiment, a plurality of suction holes 86 are provided in the proximal end portion of the probe 3 in the arrangement of the second embodiment (FIG. 3) to allow a first suction passage 21 in the probe 3 to communicate with a second suction passage defined between the outer periphery of the probe 3 and an inner sheath section 22a of a sheath 22.

This arrangement can obviate the need of providing a second suction connector 28 for a dedicated purpose and second suction tube 30 which are connected to the second suction passage 26. It is thus possible to obtain compact treatment apparatus of a simple structure.

Figure 9:
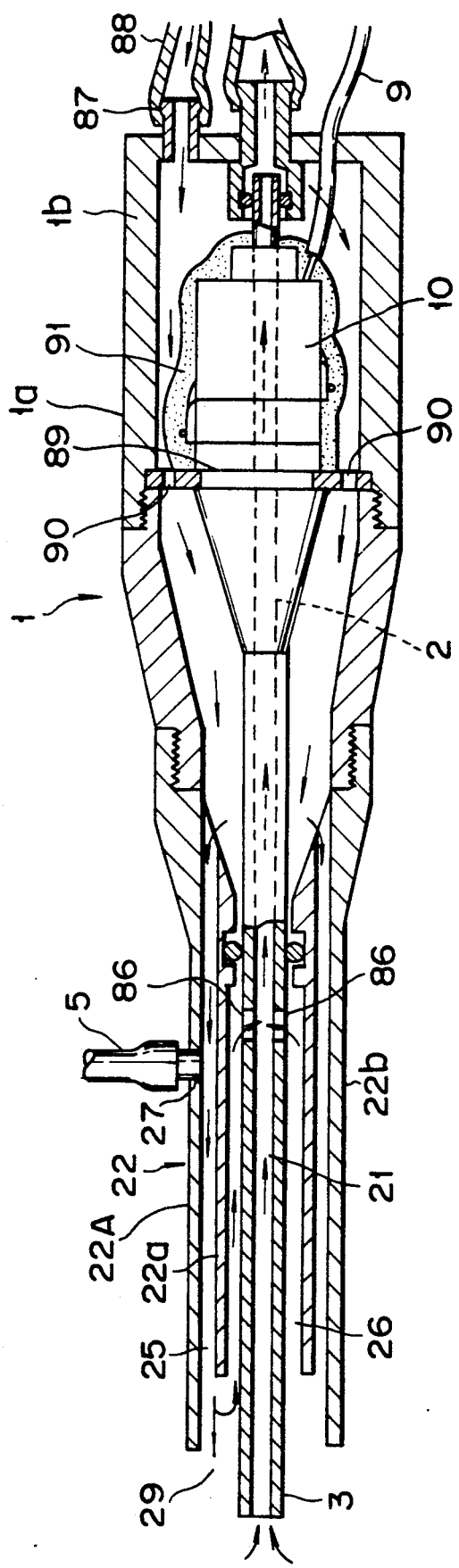
FIG. 9 is a cross-sectional view showing an ultrasound type treatment apparatus according to a seventh embodiment of the present invention.

FIG. 9 shows a seventh embodiment of the present embodiment. In this embodiment, some water is supplied via the inside of a cover 1b of a grip section 1a of a handpiece 1 into a water supply passage 25 in the arrangement of the sixth embodiment (FIG. 8). A second water supply connector 87 is fitted into the rear end wall of the cover 1b and a second water supply tube 88 is connected to the second water supply connector 87. A plurality of communication holes 90 are provided in a flange 89 of a horn 2 for water supply. The inside of the cover 1b of the grip section 1a communicates with the water supply passage 25 of a sheath 22. It is to be noted that a water-tight material 91 is covered around an ultrasonic oscillation device 10.

In the arrangement as set out above, the water can be supplied into the inside of the grip section 1a of the handpiece 1 via the second water supply tube 88 and second water supply connector 87 to allow the ultrasonic oscillation device 10 in the cover 1b to be cooled. Further, water can be supplied via the inside of the grip section 1a of the handpiece 1, allowing the probe 3 to be cooled with more water.

Figure 10:
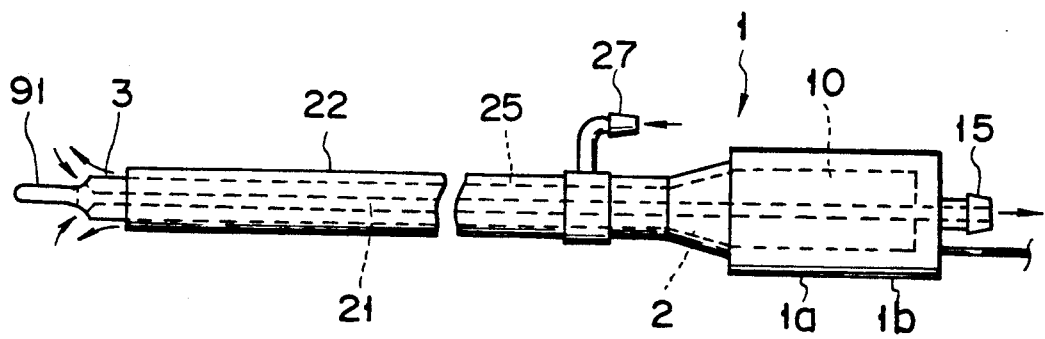
FIG. 10 is a side view showing an ultrasound type treatment apparatus according to an eighth embodiment of the present invention.
Figure 11:
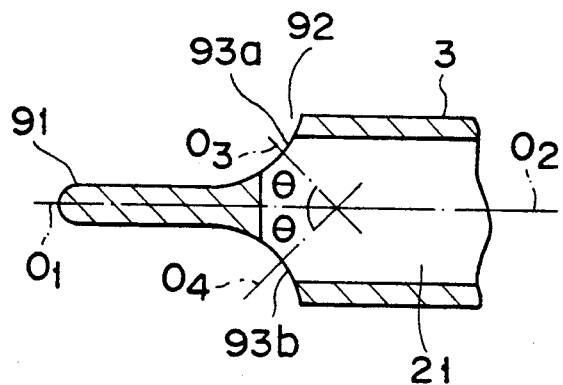
FIG. 11 is an enlarged, cross-sectional view showing a major portion of the apparatus of FIG. 10.
Figure 12:
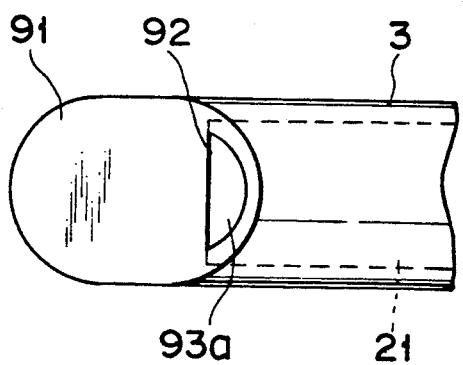
FIG. 12 is a side view of the major portion of FIG. 11.

FIGS. 10 to 12 show an eighth embodiment of the present invention.

A substantially flat-like projection 91 is provided integral with the distal end of a probe 3 of a handpiece 1 (FIG. 10) so as to separate a united tissue or remove a mucous tissue of a human being. In the arrangement shown in FIG. 11, the flat-like projection 91 has a center axis $O_1$ which aligns with a center axis $O_2$ of the probe 3. The projection 91 is made thicker at the base end that at the distal end, that is, is continuously increased in thickness partway of its axial length toward the base end.

A pair of openings 93a, 93b are provided at a boundary area between the projection 91 and the probe 3, that is, at both the sides of the projection 91 as shown in FIG. 12, to allow these openings to communicate with a suction passage 21. Here, the openings 93a and 93b have their center axes $O_3$ and $O_4$ diagonally extending relative to the center axis $O_2$ of the probe 3, that is, their center axes $O_3$ and $O_4$ intersected with respect to each other at a predetermined set angle $\theta$ on the center axis $O_2$ of the probe 3.

At the time of diagnostic treatment, the distal end of the projection 91 which is provided on the distal end of the probe 3 can be brought into contact with an affected tissue of a human being and can separate a united tissue or remove a mucous tissue by applying an ultrasonic oscillation to the tissue. At this time, cooling water, while cooling the probe 3 raised in temperature by the ultrasonic oscillation, is supplied through the water supply passage 25 of the sheath 22 into the body cavity and is drawn, together with fragments of emulsified or resected tissue and body fluid, back into an outside via the suction passage 21.

In this arrangement, since the projection 91 is made thicker at the base end than at the distal end, it is possible to provide a larger cross-sectional area at a joint between the projection 91 and the probe 3, and hence to reduce a transmission loss of ultrasonic oscillation. Further, the projection 91 ensures a firmer and more durable structure. It is also possible to provide the ultrasonic oscillation device 10 with a relatively large amplitude and hence to further enhance a treatment efficiency of treatment.

The handpiece 1 can be driven with high efficiency since as many echoes of ultrasonic oscillation as possible can be reduced at the distal end of the probe 3. A high operability can also be gained due to the thinner distal end portion of the probe 3. As the openings 93a and 93b are provided with their center axes 93a and 93b diagonally intersected on the center axis $O_2$ of the probe 3, the opening areas of the openings 93a and 93b can be made larger than when the openings 93a and 93b are so formed at both sides of the projection 91 as to be in parallel with the center axis of the projection 91. It is thus possible to prevent the fragments of a resected tissue from being caught at the openings 93a and 93b.

Figure 13:
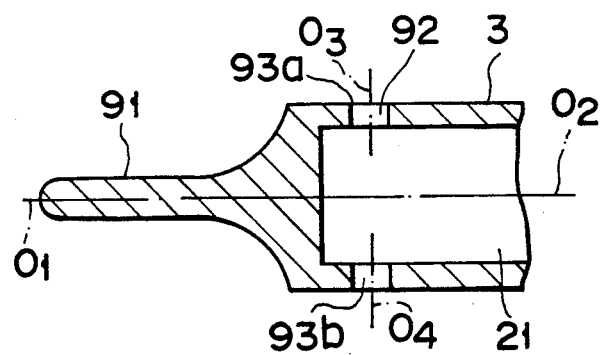
FIG. 13 is an enlarged, cross-sectional view showing a major portion of a ninth embodiment of the present invention.

FIG. 13 shows a ninth embodiment of the present invention.

In this embodiment, those openings 93a and 93b at the projection 91 of the eighth embodiment (FIG. 10 to 12) are provided at the end portion of a probe 3 with their center axes $O_3$ and $O_4$ intersected at an angle perpendicular to the center axis $O_2$ of the probe 3. The other basic arrangement and function are the same as those of the eleventh embodiment.

Here, the number, position, shape, size etc., of the openings 93a and 93b can freely be selected irrespective of the shape of the projection 91. Further, the projection 91 can be rigidly secured to the probe 3 because no gap is left at a boundary between the projection 91 and the probe 3. It is also possible to provide a firm structure to the projection 91 with less transmission loss of ultrasonic oscillation.

Figure 14:
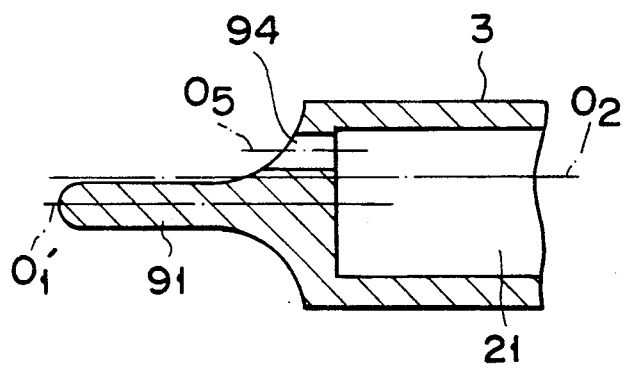
FIG. 14 is an enlarged, cross-sectional view showing a major portion of a tenth embodiment of the present invention.

FIG. 14 shows a tenth embodiment of the present invention.

In this embodiment, the projection 91 at the eighth embodiment (FIGS. 10 to 12) is provided parallel to a center axis $O_2$ of a probe 3 in an eccentric fashion with the center axis $O_1$' of the projection 91 run parallel to the center axis $O_2$ of the probe 3. Further, an opening 94 is provided at a boundary between the projection 91 and the probe 3 to communicate with a suction passage 21 with the center axis $O_5$ of the opening 94 extending in parallel with that of the probe in an eccentric fashion. The other arrangement and function of the thirteenth embodiment are the same as those of the eighth embodiment.

In the tenth embodiment, a single opening 94 having a greater opening area than the counterpart of the eighth embodiment can be provided at a boundary between the projection 91 and the probe 3.

Figure 15:
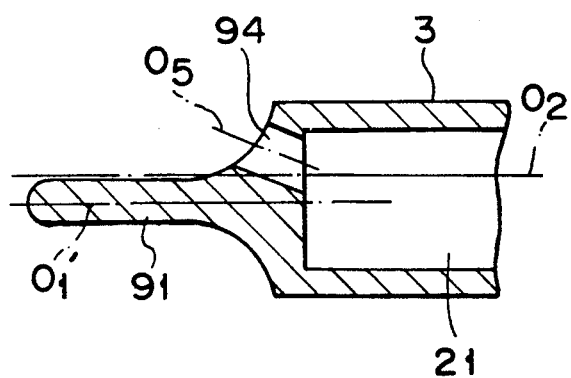
FIG. 15 is an enlarged, cross-sectional view showing a major portion of an eleventh embodiment of the present invention.

FIG. 15 shows an eleventh embodiment of the present invention.

In the eleventh embodiment, the center axis $O_5$ of the opening 94 at the tenth embodiment (FIG. 14) is diagonally intersected on a center axis $O_2$ of the probe 3 in which case it is possible to enlarge the opening area of the opening 94.

The present invention is not restricted to the aforementioned embodiment. For example, the projection 91 may have its distal end so formed as to have a blunt configuration, surgical knife configuration or a serrated configuration.

Various modifications of a distal end configuration of a probe in the diagnostic apparatus will be set forth below.

In a modification shown in FIG. 16, a large number of holes 101 are provided substantially at an equal interval and diameter in an axial length of a probe 3. Further, a liquid supply passage 102 is formed at a spacing between the probe 3 and a sheath 22 surrounding the probe 3 with the liquid supply passage 102 communicating with a suction hole 21 (a tubular hole) of the probe 3 via the holes 101 of the probe 3.

In this modification, when a larger quantity of water is supplied through the liquid supply passage 102, some of it can be drawn via the holes 101 into a suction passage 21, thus reducing that quantity of water which is released via the opening of the distal end of the sheath 22. It is thus possible to prevent an accumulation of too much of water, or the flushing of water, in a body cavity of a human being and hence to prevent a lowered field of vision and a subsequent inefficient diagnostic treatment.

FIG. 17 shows another modification in which a larger number of holes 101 are provided at varied intervals in the wall of a probe 3, that is, at a closer density toward the distal end of the probe 3 than at the other section of the probe 3. As a result, more water is drawn into a water suction passage 21 as the water is moved toward the distal end of the probe 3. It is possible to secure a proper quantity of water up to the distal end of the probe 3 and hence to uniformly cool the probe 3 throughout a whole length.

FIG. 18 shows another modification in which a larger number of holes 101 are provided at a substantially equal interval in an axial wall of a probe 3. In this modification, the diameters of the holes 101 are increased toward a distal end of the probe 3. In this modification, more water is drawn into water suction passage 21 as water is moved toward the distal end of the probe 3. This modification can obtain the same advantages as those set forth above in connection with the preceding modification.

Figure 19:
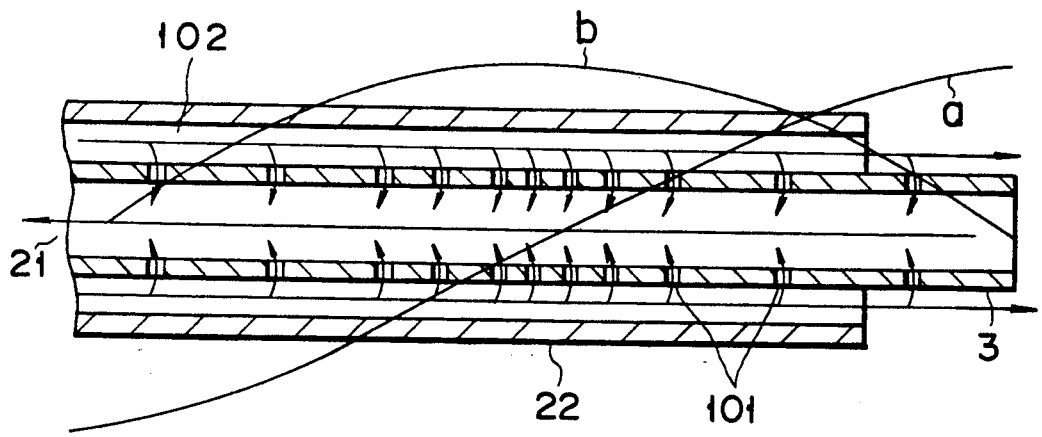

FIG. 19 shows a modification in which a larger number of holes 101 are provided in an axial wall of a probe 3 with more holes 101 arranged at a higher density substantially at an ultrasonic oscillation wave's node than in those areas not including the node. In FIG. 19, a represents the amplitude of the oscillation wave and b a stress distribution of the probe 3.

This arrangement efficiently absorbs a heat generation resulting from a stress at and near the probe's node and hence prevents a temperature rise.

A hole 101 of a greater size may be provided substantially at the node of the probe 3 instead of such denser array of holes 101 as shown in FIG. 19. A larger number of holes 101 having a larger size may be provided at a higher density substantially at the node of the probe 3.

Figure 20:
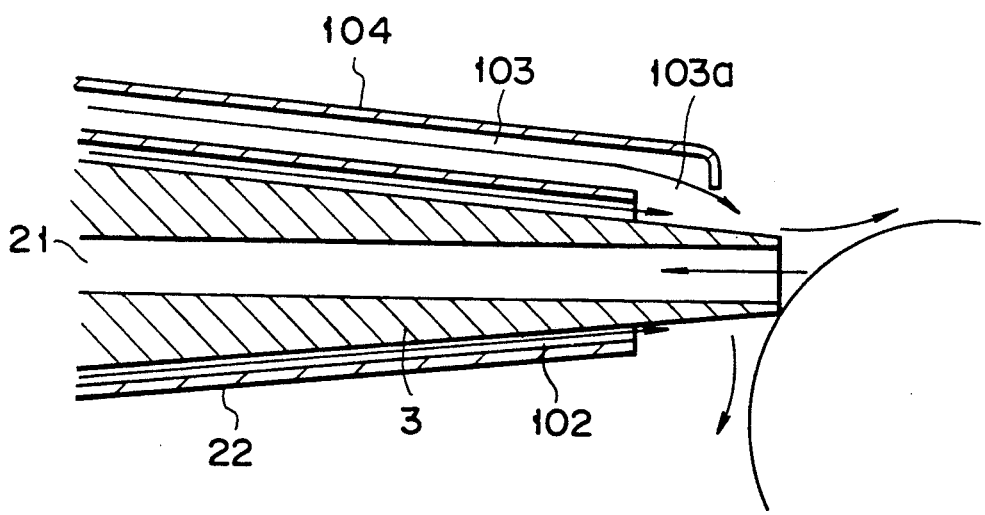

FIG. 20 shows another modification in which a water supply passage 102 is formed between the probe 3 and a covering sheath 22, and a member 104 is provided outside the sheath 22 to provide a gas supply passage 103 along the water supply passage 102. In the modification of FIG. 20, the distal end 103a of the gas supply passage 103 is opened toward the side edge of the distal end of a probe 3. The probe 3, sheath 22 and member 104 have their distal ends all tapered toward a center axis of the probe 3.

According to the present invention, it is possible to cool a water stream in the water supply passage 102, and hence to cool the probe 3, because the gas supply passage 103 is provided outside the sheath 22. Further, water intruding into a visual field of observation is displaced away from that site to provide a better field of observation.

It is also possible to secure a clean field of vision at a region of interest of a human being because the distal end portions of the probe 3, sheath 22 and member 104 are all formed as a tapered end portion each.

Figure 21:
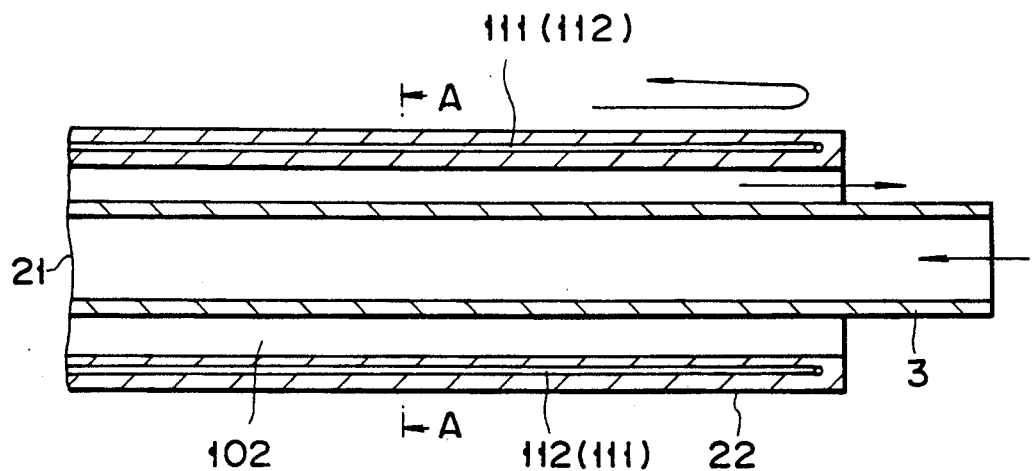
Figure 22:
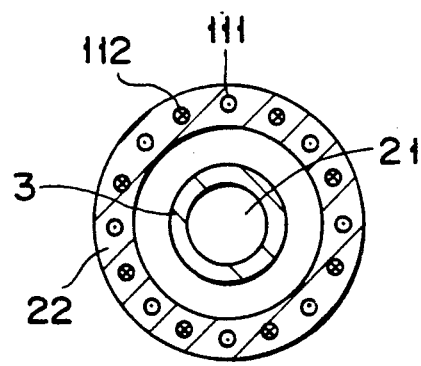
FIG. 22 is a cross-sectional view as taken along line A—A in FIG. 21.

FIGS. 21 and 22 show another modification in which water passages 111 and suction passages 112 are provided, as many sets, in the axial wall of a sheath 22 for covering a probe 3. In this modification, the forward end of the water supply passage 111 communicates with that of the associated suction passage 112 to draw a stream of cooling water through the suction passage 112. A water supply passage 102 is also formed in a spacing between the probe 3 and the sheath 22.

This arrangement can cool the sheath 22 per se because the water supply passages 111 and suction passages 112 are provided as many combination sets. It is thus possible to prevent heat which is generated at the probe 3 from being transmitted to an outside.

Figure 23:
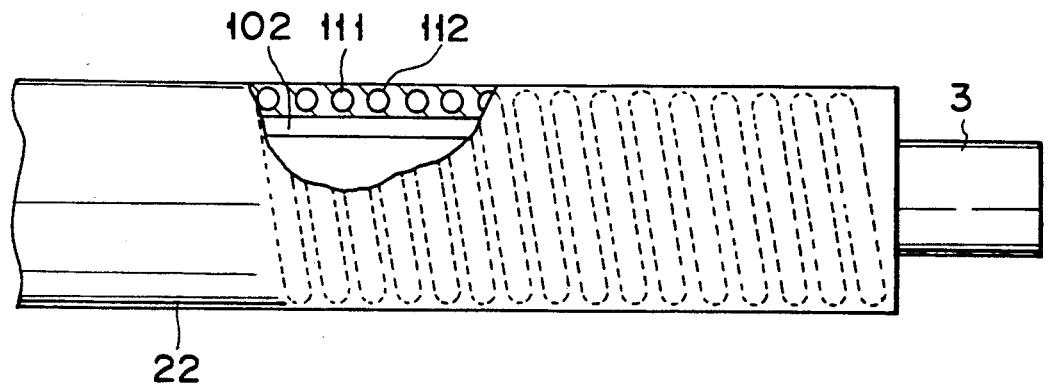
FIGS. 23 to 25, each, are a side view showing a distal end portion of a probe in a modification of the ultrasound type treatment apparatus.

FIG. 23 shows another modification of the present invention. In this modification, a water passage 111 and suction passage 112 are helically provided with the center axis of a sheath 22 as a center. The forward end of the water supply passage 111 communicates with that of the suction passage 112. A cooling water stream in the water supply passage 111 is drawn through the suction passage 112. A water supply passage 102 is formed in a spacing between a probe 3 and the sheath 22.

The sheath 22 per se can be cooled by the water supply passage 111 and suction passage 112 providing a spiral array. It is possible to prevent heat which is evolved at the probe 3 from being transmitted to an outside.

Figure 24:
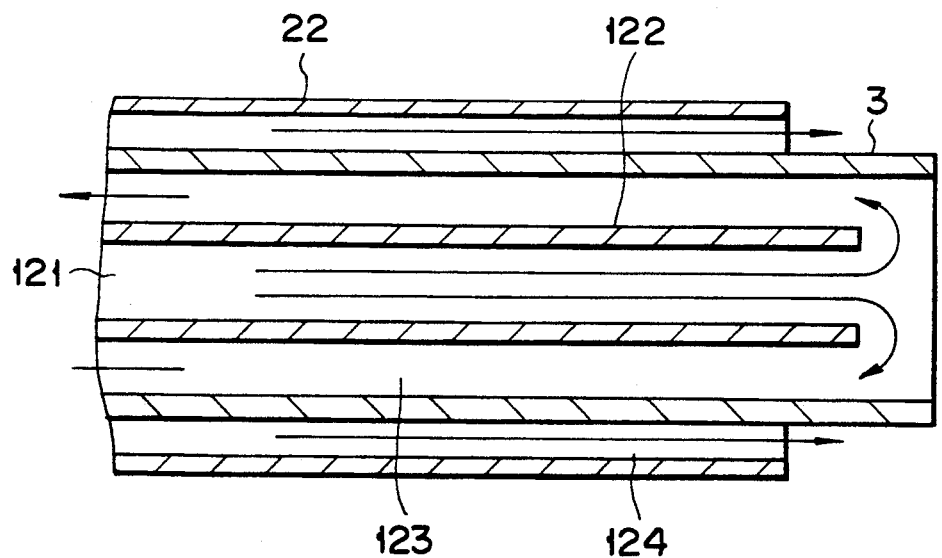

FIG. 24 shows another modification of the present invention. In the modification shown in FIG. 24, a water supply tube 122 is provided, as a water supply passage 121, in a hollow hole of a probe 3. A suction passage 123 is provided between the probe 3 and the water supply tube 122. A sheath 22 is provided outside the probe 3 and a second water supply passage 124 is formed between the probe 3 and the sheath 22. The water supply tube 122 is made shorter in length than the probe 3 as viewed from the distal end of the probe.

According to this modification, some of a water stream in the water supply passage 121 of the probe 3 can be drawn through the suction passage 123. A larger amount of water need not be supplied toward a visual field of observation at the distal end of the probe 3, ensuring a better field of observation.

Figure 25:
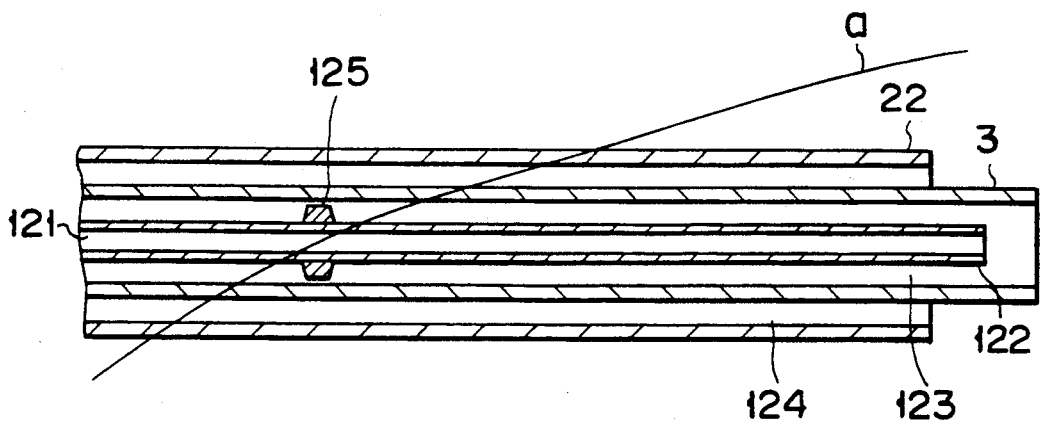
Figure 26:
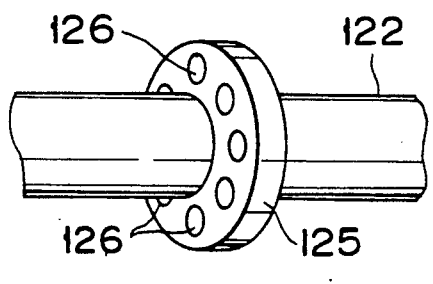
FIGS. 26 and 27, each, are a perspective view showing a flange portion for supporting a water supply tube in a modification of the treatment apparatus.

FIGS. 25 and 26 show another modification of FIG. 24. In the arrangement shown in FIGS. 25 and 26, a flange 125 is provided partway on a water supply tube 122 such that it supports the supply tube 122 at an axial center of the probe 125. The flange 125 is located substantially at the oscillation wave's node of the probe 3 and has a larger number of through holes 126 as shown in FIG. 26 to provide passages.

Figure 27:
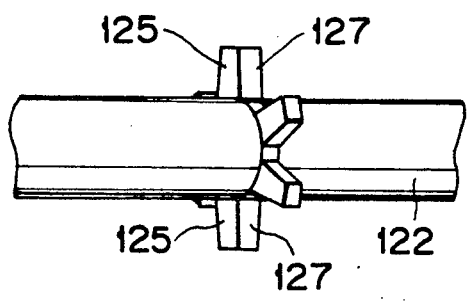

A larger number of grooves 127 may be provided, as shown in FIG. 27, in a flange 125 in place of through holes 126 of the flange shown in FIG. 26 to provide passages.

FIG. 28 shows another embodiment of the present invention. In this embodiment, the hole of a probe 3 provides a suction passage 131 and a helical water supply tube 132 is arranged in a suction passage 131 of the probe 3 in a concentric fashion. A second water supply passage 133 may be provided between the probe 3 and a sheath 22.

The distal end of the water supply tube 132 is located in the suction passage 131 at a location short of the distal end of the probe 3, that is, without being projected from the distal end of the probe 3.

This arrangement allows some of water which is supplied from the water supply tube 132 to be drawn through the suction passage 131, obviating the need of supplying more water toward a visual field of observation. It is possible to secure a better field of observation. Further, the length of the water supply tube 132 can be adjusted in accordance with the length of the probe 3, because the water supply tube 132 has such a helical structure as shown in FIG. 28.

FIG. 29 shows another modification of the present invention. This modification is similar to the modification shown in FIG. 24 except that a water supply tube 122 has a larger number of water supply holes 141.

This arrangement can uniformly cool a probe 3 as a whole.

The arrangement as set out above can be applied to those having a water supply passage in a probe 3.

Figure 30:
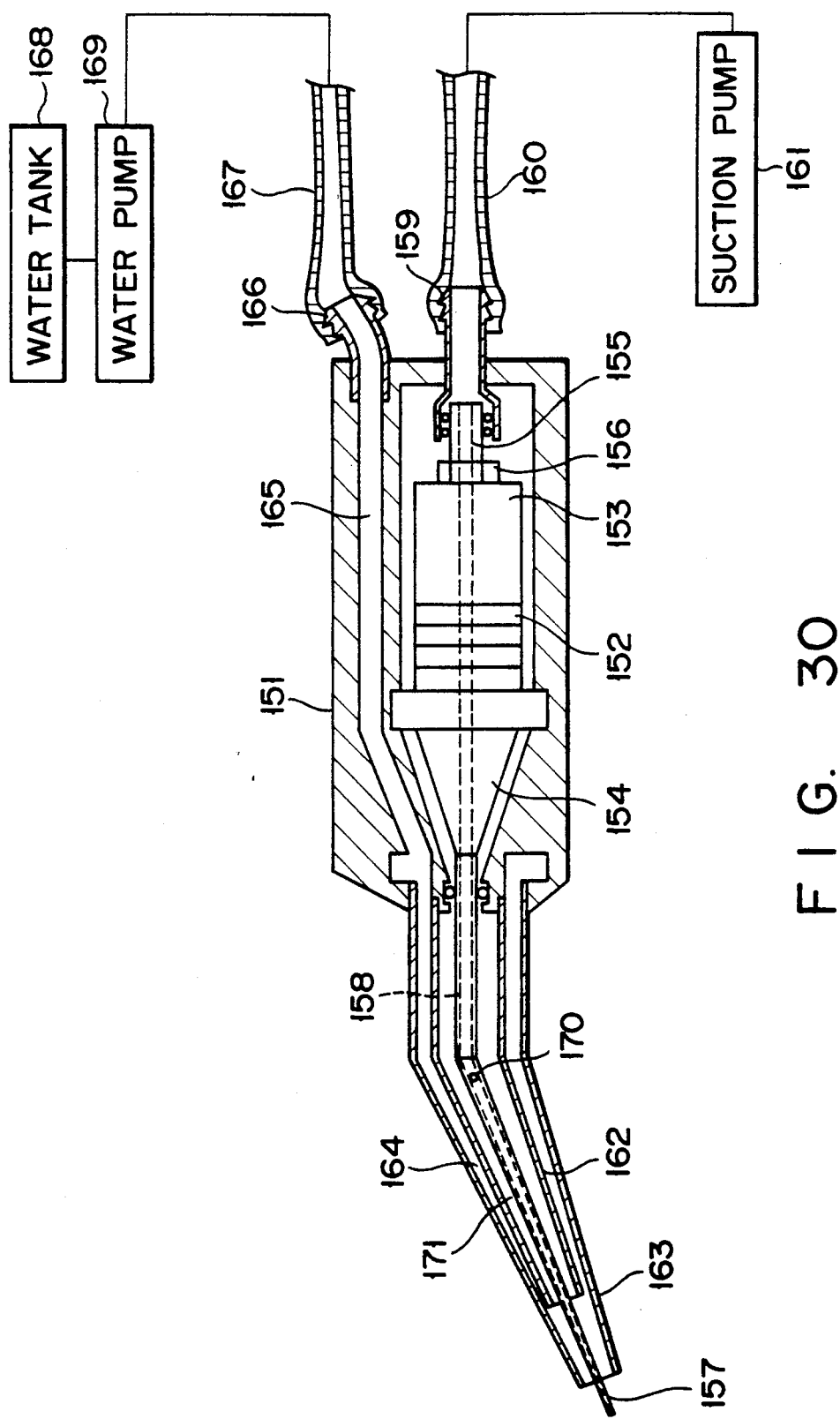
FIG. 30 is a side view in cross-section generally showing an ultrasound type treatment apparatus according to a twelfth embodiment of the present invention.

FIG. 30 shows a twelfth embodiment of the present embodiment.

In this embodiment, reference numeral 151 represents a cover providing a grip section of a handpiece. An ultrasonic oscillation element 152 is held in the cover 151. The ultrasonic oscillation element 152 is comprised of a plurality of piezoelectric elements. A back-up plate 153 is provided at the back end of the ultrasonic oscillation element 152 to provide a resonance balance. A horn 154 is provided at the forward end of the ultrasonic oscillation element 152 so as to amplify the ultrasonic oscillation.

The horn 154, ultrasonic oscillation element 152 and back-up plate 153 are mounted as one unit by means of a bolt 155 and nut 156. A tubular, ultrasound transmission member (probe) 157 is provided at the distal end of the horn 154 to transmit the ultrasonic oscillation to an affected or diseased region of the human being. The ultrasound transmission member 157 tapers toward the distal end 157 and is bent partway at a proper angle.

A suction passage 158 is provided in the ultrasound transmission member 157, horn 154 and bolt 155 so as to suck a diseased tissue emulsified by the ultrasound oscillation and a fractured stone, etc. The suction passage 158 is connected to a suction connector 159 provided at the rear end of the cover 151. A suction tube 160 is connected to the suction connector 159 to remove, to an outside, the emulsified living tissue, fractured stone, etc., by a suction force of the suction pump 161.

An inner sheath 162 and outer sheath 163 are provided outside the ultrasound transmission member 157 to cover the ultrasound transmission member 157. The rear ends of the inner sheath 162 and outer sheath 163 are connected to the forward end of the cover 151. A water supply passage 164 for supplying a perfusion liquid is provided at an ultrasonic treatment section between the inner sheath 162 and the outer sheath 163.

The water supply passage 164 is connected to through a water supply passage 165 in the cover 151 to a water supply connector 166 provided at the rear end of the water supply passage 165. A water supply tube 167 is connected to the water supply connector 166. A water supply pump 169 connected to a water supply tank 168 is connected to the water supply tube 168. The perfusion liquid is supplied from the water supply pump 169 via the water supply tube 167, water supply connector 166 and passages 165 and 164 to the distal end of the outer sheath 163 and flowed out of the distal end of the outer sheath.

A leak hole 170 is provided at the rear end portion of the ultrasound transmission member 157 to enable a space between the inner sheath 162 and the ultrasound transmission member 157 to be connected to the suction passage 158. The leak hole 170 is located near the rear end portion of a bending section of the ultrasound transmission member 157. The leak hole 170 is provided at the loop of the oscillation of the ultrasound transmission member 157 to make a stress at a time of ultrasound oscillation minimal. A second suction passage 171 is provided for transmitting a suction force from the leak hole 170 to the open distal end of the inner sheath 162 via the space between the inner sheath 162 and the ultrasound transmission member 157. Some of the perfusion liquid supplied to the spacing between the inner sheath 162 and the outer sheath 163 is turned back near the distal end of the inner sheath 162, sucked from the opened distal end of the inner sheath 162 into the second suction passage 171 and flowed in the second suction passage 171 and from the leak hole 170 into the suction passage 158. The distal end of the outer sheath 163 is more projected than the distal end of the inner sheath 162.

In the aforementioned ultrasound type treatment apparatus, some of the perfusion liquid supplied to an area between the inner sheath 162 and the outer sheath 163 is turned back near the distal end of the inner sheath 162 by the suction force of the leak hole 170 provided at the base end portion of the bending section of the ultrasound transmission member 157 and flowed in the second suction passage 171 between the inner sheath 162 and the ultrasound transmission member 157. It is, therefore, possible to cool substantially a full length of the ultrasound transmission member 157. Since, therefore, the cooling effect of the ultrasound transmission member 157 and ultrasonic oscillation element 152 can be enhanced, it is possible to prevent the heat generation in the ultrasound oscillation element 152 and destruction of the ultrasound transmission member 157 due to a fatigue involved.

The atomizing of the perfusion liquid can be prevented by controlling the amount of perfusion liquid supplied and suction force of the leak hole 170. This enables a surgical operation to be performed by an ultrasonic wave under a better visual field.

Figure 31:
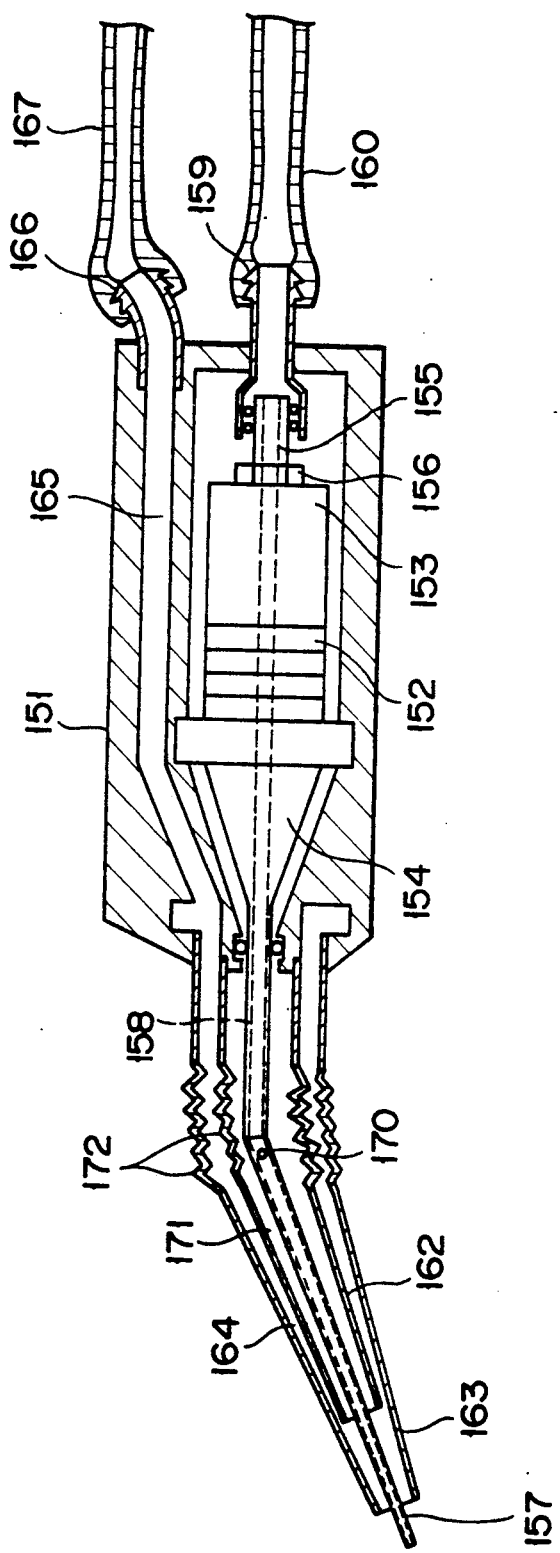
FIG. 31 is a side view in cross-section generally showing an ultrasound type treatment apparatus according to a thirteenth embodiment of the present invention.

FIG. 31 shows a thirteenth embodiment of the present invention.

In this embodiment, bellows 172 are provided at the intermediate portion of the inner sheath 162 and outer sheath 163 of the twelfth embodiment shown in FIG. 30. This arrangement gives an added flexibility to the inner sheath 162 and outer sheath 163 and ensures ready attachment and detachment of the inner sheath 162 and outer sheath 163 at the time of an attachment and detachment.

Figure 32:
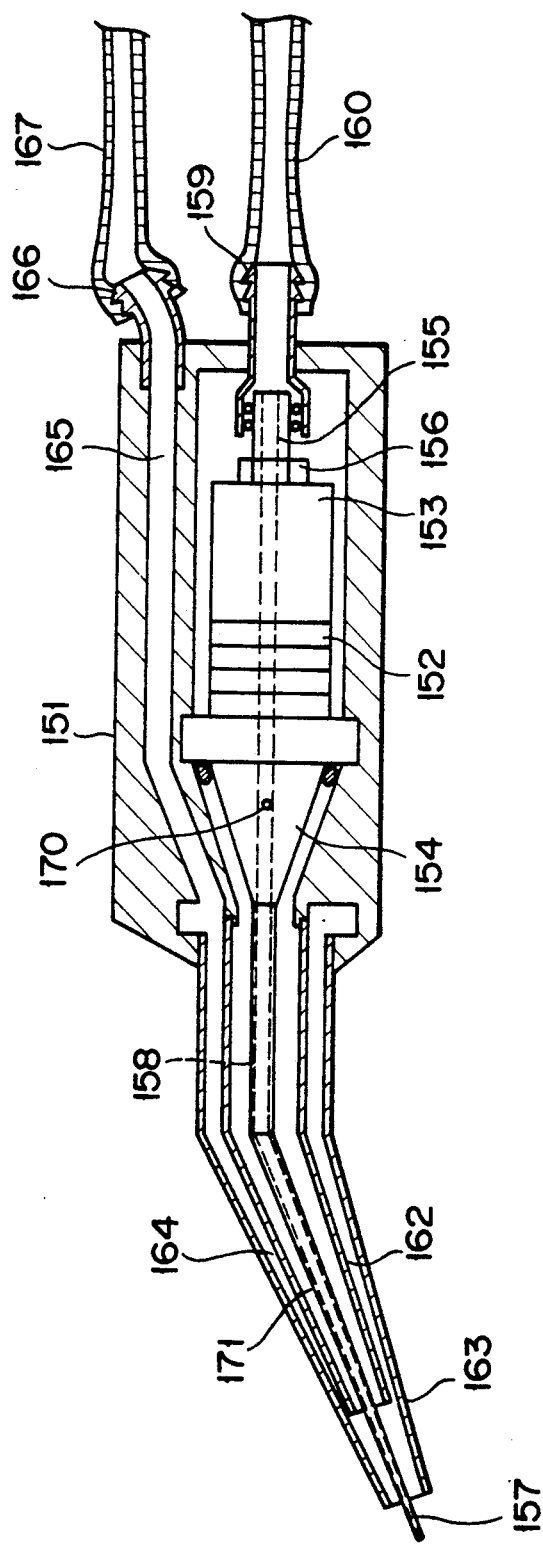
FIG. 32 is a side view in cross-section showing a fourteenth embodiment of the present invention.

FIG. 32 shows a fourteenth embodiment of the present invention.

The second suction passage 171 of the twelfth embodiment (FIG. 30) extends over the outer peripheral surface of the horn 154 and a leak hole 170 is provided in the horn 154.

Figure 33:
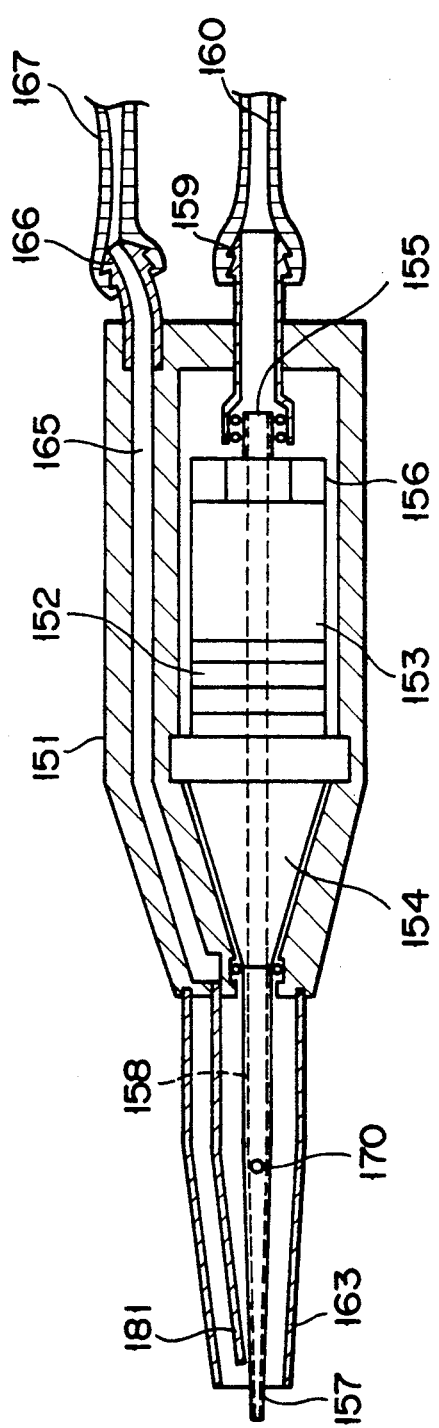
FIG. 33 is a side view in cross-section generally showing an ultrasound type treatment apparatus according to a fifteenth embodiment of the present invention.
Figure 34:
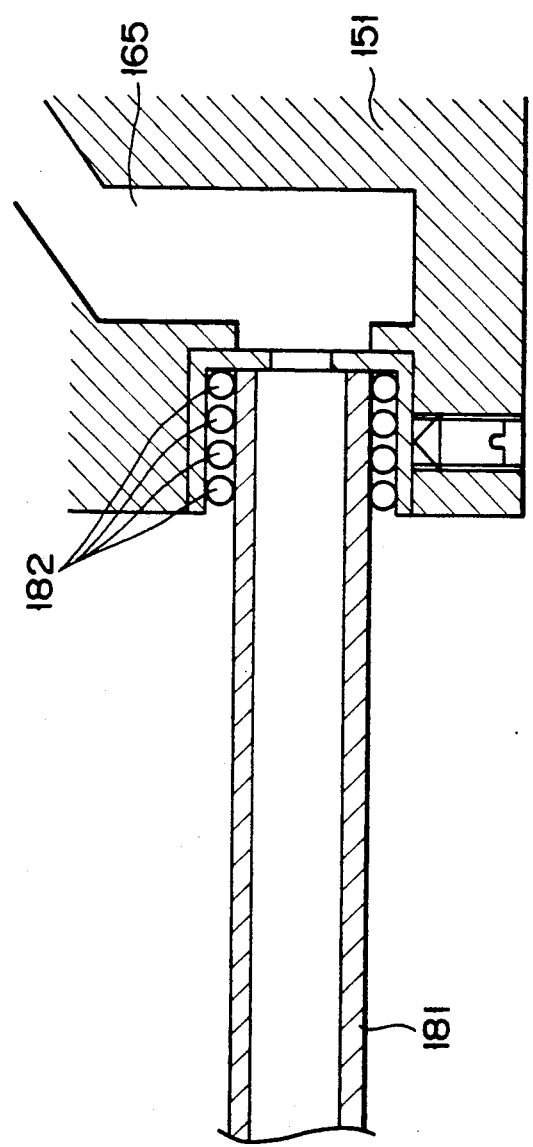
FIG. 34 is a side view in cross-section showing a connection area between a water supply tube and a cover in the aforementioned embodiment.

Although, in the twelfth embodiment (FIG. 30), the inner sheath 162 is provided inside the outer sheath 163, a water supply tube 181 is provided inside the outer sheath 163 as in the fifth embodiment (FIG. 33) of the present invention and, as shown in FIG. 34, the rear end of the water supply tube 181 may be fixedly connected to a water supply passage 165 of a cover 151 by an elastic force of an elastic member 182, such as a coil spring.

Figure 35:
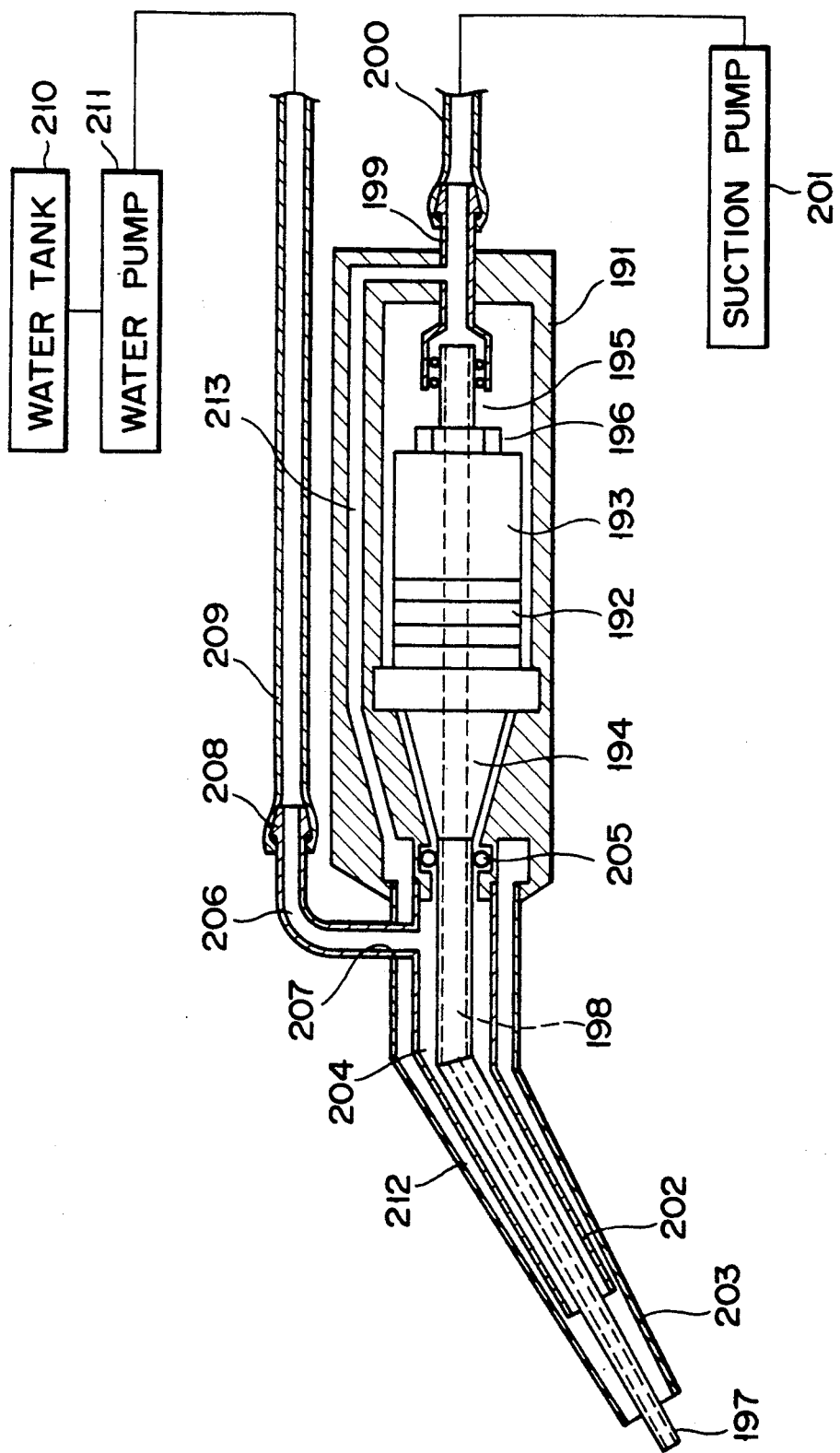
FIG. 35 is a side view in cross-section generally showing an ultrasound type treatment apparatus according to a sixteenth embodiment of the present invention.

FIG. 35 shows a sixteenth embodiment of the present invention.

In the embodiment shown in FIG. 35, reference numeral 191 shows a cover serving as a grip of a handpiece. An ultrasonic oscillation element 192 is held in the cover 191 and comprised of a plurality of piezoelectric elements. A back-up plate 193 for taking a resonance balance is provided at the rear end of the ultrasonic oscillation element 192. A horn 194 is provided at the forward end of the ultrasonic oscillation element 192 so as to amplify the ultrasonic oscillation.

The horn 194, ultrasonic oscillation element 192 and back-up plate 193 are provided as one unit by means of a bolt 195 and nut 196. A tubular, ultrasonic transmission member (probe) 197 is provided at the forward end of the horn 194 so as to transmit the ultrasonic oscillation to an affected or diseased region of the human being. The ultrasound transmission member 197 is narrowed toward its distal end with the intermediate area of the member 197 bent at a proper angle.

A suction passage 198 is provided in the ultrasound transmission member 197, horn 194 and belt 195 so as to suck the diseased tissue emulsified, and a stone fractured, by the ultrasonic oscillation. The suction passage 198 is connected to a suction connector 199 provided at the rear end of the cover 191. A suction tube 200 is connected to the suction connector 199. The suction tube 200 is connected to a suction pump 201. The emulsified living tissue, fractured stone, etc., are externally removed by the suction force of the suction pump 201.

A double tube comprised of an inner sheath 202 and outer sheath 203 is so provided outside the ultrasound transmission member 197 to cover the ultrasound transmission member 197, the double tube being made of an elastic material, such as Teflon (trade name). The inner sheath 202 and outer sheath 203 may be made of, for example, silicon, polyurethane, etc. The inner sheath 202 and outer sheath 203 may be of such a type that at least their bending sections and those areas near them are flexible. In this case, the remaining portions may be formed of a rigid material, such as polysulfone.

The inner sheath 202 and outer sheath 203 are connected at their rear ends to the forward end of the cover 191. A water supply passage 204 for supplying a perfusion liquid to the ultrasound type treatment apparatus is defined between the inner sheath 202 and the ultrasound transmission member 197. A sealing member 205, such as an O ring, is provided at the base end side of the water supply passage 204, preventing water in the water supply passage 204 from flowing back toward the ultrasonic oscillation element 192.

A connection tube 206 is connected at one end to the base end of the inner sheath 202. The other end of the connection tube 206 extends to an outside of the outer sheath 203 via a tube connector 207 of the outer sheath 203. The water supply connector 208 is provided at that extending end of the connection tube 203. A water supply tube 209 is connected to the water supply connector 208. A water supply pup 211 is connected to the water supply tube 209 and to the water supply tank 210. A perfusion liquid supplied from the water supply pump 211 to the water supply tube 209 is flowed out of the distal end of the inner sheath 202 past the water supply connector 208, connection tube 206 and water supply passage 204.

A second suction passage 212 is defined between the inner sheath 202 and the outer sheath 203 and connected to the suction connector 199 through a connection passage 213 in the cover 191. A suction force from the suction connector 199 is transmitted to the forward end side of the second suction passage 212 through the connection passage 213 and second suction passage 212. Some of the perfusion liquid supplied to the water supply passage 204 is sucked back into the second suction passage 212 at an area near the distal end of the inner sheath 202 and flowed past the second suction passage 212 and connection passage 213 and then past the suction connector 199 into the suction passage 198. The distal end of the outer sheath 203 is more projected than that of the inner sheath 202.

In the ultrasound type treatment apparatus thus arranged, some of the perfusion liquid supplied into the water supply tube 204 defined between the inner sheath 201 and the ultrasound transmission member 197 is turned back, by a suction force from the second suction passage 212, at an area near the inner sheath 202 and flowed past the second suction passage 204 between the inner sheath 202 and the outer sheath 203, past the connection passage 213 and past the suction passage 198 into the suction passage 198. It is, therefore, possible to cool substantially the full length of the ultrasound transmission member 197 with the perfusion liquid. That is, it is possible to enhance the cooling effect of the ultrasound transmission member 197 and ultrasound oscillation element 192 and hence to prevent the generation of heat in the ultrasonic oscillation element 192 and destruction of the ultrasound oscillation element 192 due to a fatigue involved.

Since it is not necessary to provide any leak hole in the ultrasound transmission member 197, a fall in the mechanical strength of the ultrasound transmission member 197 can be prevented, thus ensuring an enhanced durability of the ultrasound transmission member 197.

By controlling the amount of perfusion liquid and suction force, it is possible to properly control an amount of perfusion liquid, while maintaining the cooling effect of the ultrasound transmission member, which is discharged out of the distal end of the outer sheath 203. Since the atomizing of the perfusion liquid can be prevented, a surgical operation can be performed, by an ultrasonic wave, on a diseased region under a better visual field.

FIG. 36 shows a seventeenth embodiment of the present invention.

On the outer surface of the cover 191 of the sixteenth embodiment (FIG. 35), a suction pressure regulating section 221 is provided for regulating a suction force of the second suction passage 212. The suction pressure regulating section 221 has a finger receiving section 222 for receiving the finger of, for example, of the user and a communication passage 223 situated at the central area of the finger receiving section 222 and communicating with the connection passage 213. The suction force of the second suction passage 212 can be properly controlled by varying the area of the opening of the communication passage 223 by the human finger, etc., applied to the finger receiving section 222.

The aforementioned treatment apparatus can also obtain the same advantage as that of the sixteenth embodiment. Since, in this case, the user can readily control the suction force of the second suction passage 212 by regulating the operation on the suction pressure regulating section 221 of the handpiece, it is possible to improve the operability of the treatment apparatus.

Figure 37:
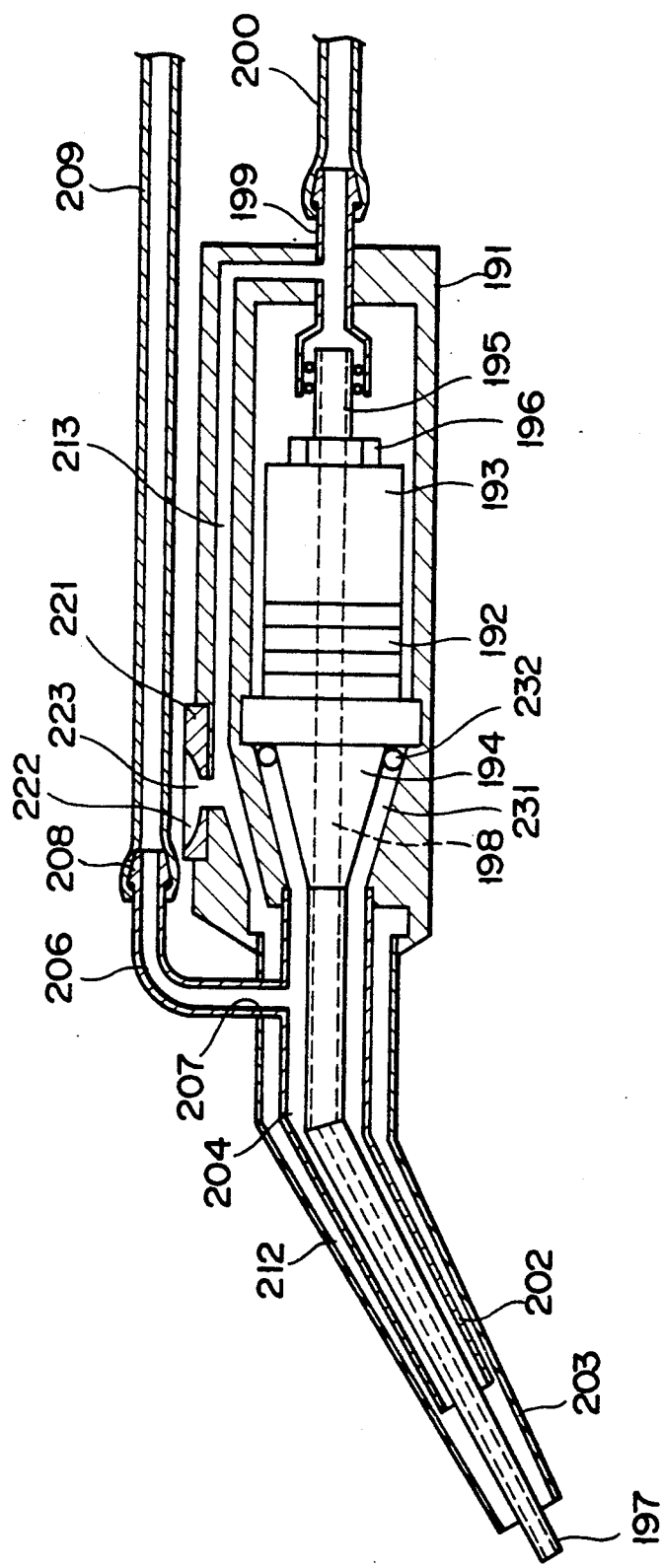
FIG. 37 is a side view in cross-section generally showing an ultrasound type treatment apparatus according to an eighteenth embodiment of the present invention.

FIG. 37 shows an eighteenth embodiment of the present invention.

The water supply passage 204 of the seventeenth embodiment (FIG. 36) has an extension section 231 extending over the outer peripheral surface of a horn 194. A sealing member 232, such as an O-ring, is provided at the base end portion of the extension section 231 such that it is placed in pressure contact with the outer periphery of the horn 194 where there is a connection area between the horn 194 and an ultrasonic oscillation element (device) 192.

It is possible, as in this embodiment, to obtain the same advantage as in the seventeenth embodiment. In this case, a perfusion liquid supplied into the water supply passage 204 is flowed over the extension section 231, enabling the horn 194, together with an ultrasound transmission member 197, to be effectively cooled. It is thus possible to prevent the destruction of the ultrasonic oscillation element 192 due to a heat involved.

Further, the flow of water in the water supply passage into the ultrasonic oscillation element 192 side can be prevented by the sealing member 232 and there is no possibility that electric current on the ultrasonic oscillation element 192 side will leak to an outside of the cover 191 of the handpiece.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An ultrasound type treatment apparatus comprising:
    ultrasonic oscillation means for generating an ultrasonic oscillation;
    amplifying means for amplifying the ultrasonic oscillation generated by the ultrasonic oscillation means;
    ultrasound transmission means, connected to a forward end of the amplifying means, and having a first suction passage therein;
    a cover member for covering an outer periphery of the ultrasound oscillation means;
    an inner sheath covering the ultrasound transmission means and defining a first space between the inner sheath and the ultrasound transmission means, the inner sheath having a base end portion thereof extending in a direction toward the ultrasonic oscillation means and a distal end portion thereof extending in a direction toward a distal end portion of the ultrasound transmission means;
    an outer sheath covering the inner sheath and defining a second space between the outer sheath and the inner sheath, the outer sheath having a base end portion extending in the direction toward the ultrasonic oscillation means and a distal end portion extending in the direction toward the distal end portion of the ultrasound transmission means;
    a liquid medium supply passage provided at one of the first and second spaces to supply a liquid medium to the distal end portion of the ultrasound transmission means; and
    diverting means for providing at least one of backing up and diverting at least a portion of the liquid medium in the liquid medium supply passage, said diverting means including:
        a second suction passage provided at the other one of the first and second spaces; and
        connecting means for connecting the first suction passage to the second suction passage to thereby provide a fluid flow path from the diverting means to the another end portion of the ultrasound transmission means to cool both the distal end portion and the another end portion of the ultrasound transmission means.

2. An apparatus according to claim 1, wherein the second suction passage comprises the first space defined between the ultrasound transmission means and the inner sheath.

3. An apparatus according to claim 2, wherein the connecting means comprises an aperture formed in a base end portion of the ultrasound transmission means.

4. An apparatus according to claim 2, wherein the connecting means comprises an aperture formed at a loop portion of an ultrasonic oscillation means of the ultrasound transmission means.

5. An apparatus according to claim 2, wherein the amplifying means comprises a suction tube positioned to be in fluid communication with the first suction passage and wherein the connecting means comprises an aperture for enabling a suction of the liquid medium, said connecting means providing a fluid path to the amplifying means.

6. An apparatus according to claim 1, wherein the inner sheath and outer sheath, each include a flexible bellows-like portion.

7. An apparatus according to claim 1, wherein the cover member has a supply passage formed therein for enabling the liquid medium which is provided by a liquid medium supply source to be supplied to the liquid medium supply passage.

8. An apparatus according to claim 1, wherein the second suction passage comprises the second space between the inner sheath and the outer sheath.

9. An apparatus according to claim 8, wherein the connecting means comprises a suction tube having a first and a second end portion, the first end portion of the suction tube being connected to the base end portion of the outer sheath and the second end portion of the suction tube being connected to the first suction passage.

10. An apparatus according to claim 8, wherein the connecting means comprises a communication passage formed in the cover member.

11. An apparatus according to claim 10, further comprising suction pressure regulating means provided at an outer surface portion of the cover member, the suction pressure regulating means having an adjustable opening in fluid communication with the communication passage so that a suction pressure can be regulated by changing a size of the adjustable opening of the suction pressure regulating means.

12. An ultrasound type treatment apparatus comprising:

ultrasonic oscillation means for generating an ultrasonic oscillation;

amplifying means having a first and a second end portion, said amplifying means amplifying the ultrasonic oscillation generated by the ultrasonic oscillation means;

ultrasound transmission means, connected to the first end portion of the amplifying means, and having a suction passage therein;

a sheath covering the ultrasound transmission means, the sheath having a base end portion, extending in a direction toward the ultrasound oscillation means and a distal end portion extending in a direction toward a distal end portion of the ultrasound transmission means;

connecting means for connecting at least one space defined between the ultrasound transmission means and the sheath, to the suction passage;

liquid medium supply means in fluid communication with the at least one space defined between the ultrasound transmission means and the sheath for supplying a liquid medium to a distal end portion of the ultrasound transmission means; and diverting means for providing at least one of backing up and diverting at least a portion of the liquid medium supplied from the liquid medium supply means to another end portion of the ultrasound transmission means, said diverting means including said connecting means.

* * * * *